US009730954B2

(12) United States Patent
Rao et al.

(10) Patent No.: US 9,730,954 B2
(45) Date of Patent: Aug. 15, 2017

(54) MIRNAS AS NOVEL THERAPEUTIC ADJUVANTS AND BIOMARKERS FOR THE PROGNOSIS AND TREATMENT OF DRUG RESISTANT BREAST CANCERS

(71) Applicant: THE BOARD OF REGENTS OF THE UNIVERSITY OF TEXAS SYSTEM, Austin, TX (US)

(72) Inventors: Manjeet K. Rao, San Antonio, TX (US); Jaafer S. Imam, San Antonio, TX (US); Behyar Zoghi, San Antonio, TX (US); Yao-Fu Chang, San Antonio, TX (US); Panneerdoss Subbarayalu, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/442,896

(22) PCT Filed: Nov. 15, 2013

(86) PCT No.: PCT/US2013/070350
§ 371 (c)(1),
(2) Date: May 14, 2015

(87) PCT Pub. No.: WO2014/078686
PCT Pub. Date: May 22, 2014

(65) Prior Publication Data
US 2015/0306127 A1    Oct. 29, 2015

Related U.S. Application Data

(60) Provisional application No. 61/727,481, filed on Nov. 16, 2012.

(51) Int. Cl.
| C12N 15/113 | (2010.01) |
| A61K 31/713 | (2006.01) |
| A61K 31/7105 | (2006.01) |
| C12Q 1/68 | (2006.01) |
| A61K 45/06 | (2006.01) |

(52) U.S. Cl.
CPC ........ *A61K 31/713* (2013.01); *A61K 31/7105* (2013.01); *A61K 45/06* (2013.01); *C12N 15/113* (2013.01); *C12Q 1/6886* (2013.01); *C12N 2310/141* (2013.01); *C12Q 2600/106* (2013.01); *C12Q 2600/158* (2013.01); *C12Q 2600/178* (2013.01)

(58) Field of Classification Search
CPC .............. C12N 15/113; C12N 2310/141
See application file for complete search history.

(56) References Cited

U.S. PATENT DOCUMENTS

2008/0261908 A1* 10/2008 Croce .................. C12Q 1/6886
514/44 R

FOREIGN PATENT DOCUMENTS

EP    2354246    8/2011

OTHER PUBLICATIONS

Au et al., "Tyrosine kinase B receptor and BDNF expression in ovarian cancers—Effect on cell migration, angiogenesis and clinical outcome." Cancer Lett. vol. 281, 2009, pp. 151-161.
Brodeur, "Neuroblastoma: biological insights into a clinical enigma." Nat Rev Cancer, vol. 3, 2003, pp. 203-216.
Edsjo et al., "Expression of trkB in human neuroblastoma in relation to MYCN expression and retinoic acid treatment." Lab Invest. vol. 83, 2003, pp. 813-823.
Enomoto et al., Dev Cell. 9:389-402, 2005.
Esquela-Kerscher et al., "Oncomirs—microRNAs with a role in cancer." Nat Rev Cancer. vol. 6, 2006, pp. 259-269.
Gong, C. et al., "Up-regulation of miR-21 mediates resistance to trastuzumab therapy for breast cancer", The Journal of Biological Chemistry, 2011, vol. 286, p. 19127-19137.
Grille et al., Cancer Res. 63:2172-2178, 2003.
Guo et al., Nature. 466:835-840, 2010.
Hanahan & Weinberg, Cell. 100:57-70, 2000.
Higuchi et al., Curr Biol 11:1958-1962, 2001.
Imam et al., Oncogene. 29:4971-4979, 2010.
International Preliminary Report on Patentability issued in PCT/US2013/070350, mailed on May 28, 2015.
International Search Report issued in PCT/US2013/070350 mailed on Feb. 27, 2014.
Kastl, L., et al., "miRNA-34a is associated with docetaxel resistance in human breast cancer cells", Breast Cancer Research and Treatment, Jan. 2012, vol. 131, p. 445-454.
Kim et al., "Selective activation of Akt1 by mammalian target of rapamycin complex 2 regulates cancer cell migration, invasion, and metastasis." Oncogene. vol. 30, 2011, pp. 2954-2963.
Krishnan et al., "Ezrin mediates growth and survival in Ewing's sarcoma through the AKT/mTOR, but not the MAPK, signaling pathway." Clin Exp Metastasis, vol. 23, 2006, pp. 227-236.
Lewin, "Neurotrophins and the specification of neuronal phenotype." Philos Trans R Soc Lond B Biol Sci., vol. 351, 1996, pp. 405-411.
Nakagawara et al., Mol Cell Biol. 14:759-767, 1994.
Qiu et al., Int J Oncol 29:1003-1011, 2006.
Ryan, J. et al., "MicroRNA-204 increases sensitivity of neuroblastoma cells to cisplatin and is associated with a favourable clinical outcome", British Journal of Cancer, Aug. 14, 2012, vol. 107, p. 967-976.
Segal et al., J Biol Chem. 271:20175-20181, 1996.
Shen et al., "The tumorigenicity diversification in human embryonic kidney 293 cell line cultured in vitro." Biologicals. vol. 36, 2008, pp. 263-268.
Siu et al., "TrkB as a therapeutic target for ovarian cancer." Expert Opin Ther Targets. vol. 13, 2009, pp. 1169-1178.

(Continued)

*Primary Examiner* — Jon E Angell
(74) *Attorney, Agent, or Firm* — Norton Rose Fulbright US LLP

(57) ABSTRACT

Disclosed are methods and compositions for using microRNA (miRNA) for treating cancer. The methods and compositions include hsa-miR-204 and homologs of hsa-miR-204.

6 Claims, 28 Drawing Sheets

(56) References Cited

OTHER PUBLICATIONS

Troca-Martin et al., "Local translation of dendritic RhoA revealed by an improved synaptoneurosome preparation." Mol. Cell Neurosci. vol. 43, 2010, pp. 308-314.
Wu, J. et al., "miR-129 regulates cell proliferation by downregulation Cdk6 expression", Cell Cycle, 2010, vol. 9(9), p. 1809-1818.
Wyckoff et al., Cancer Res. 64:7022-7029, 2004.
Zadran et al., J. Neurosci. 30:1086-1095, 2010.

* cited by examiner

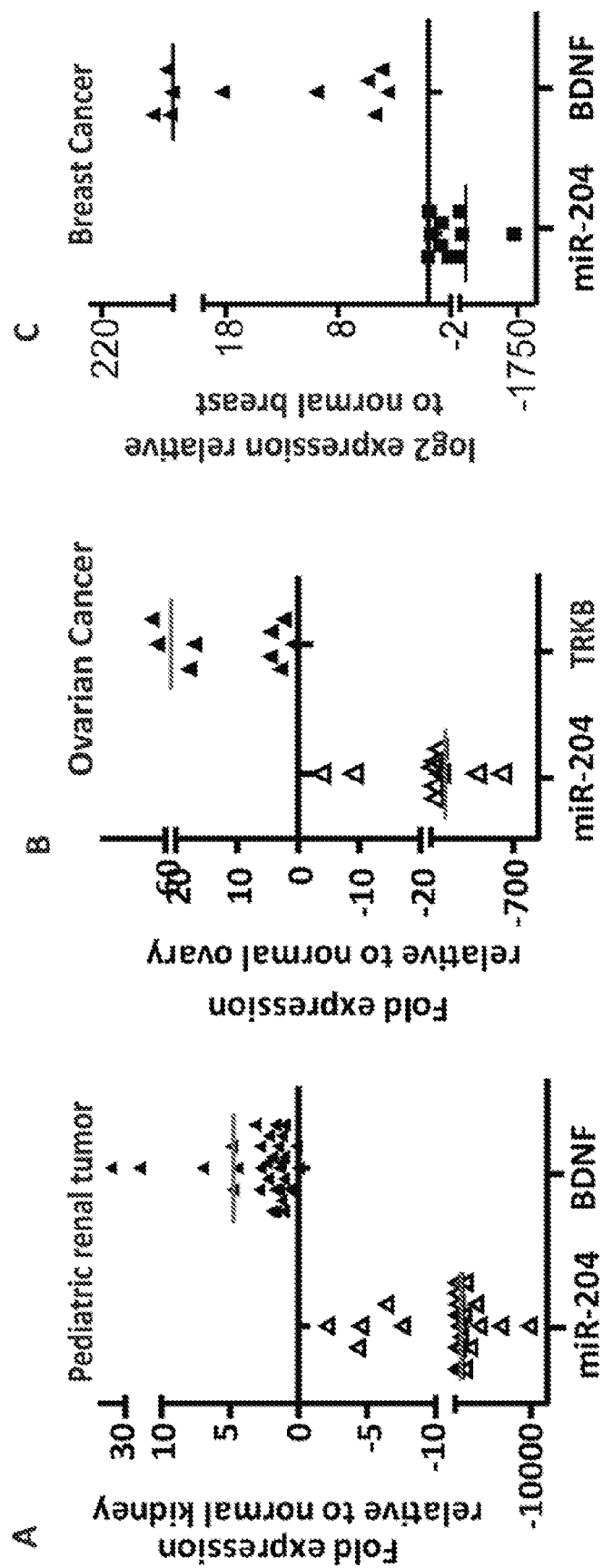
FIGS. 4A-C

| miRNA | chr | start | end | CN loss % (Ovarian Cancer) | CN loss % (Breast Cancer) | CN loss % ( Ped. Renal tumors) |
|---|---|---|---|---|---|---|
| hsa-mir-140 | chr16 | 68524484 | 68524584 | 65.81 | 51.43 | 66.67 |
| hsa-mir-220b | chr19 | 6446958 | 6447045 | 59.6 | 34.29 | 50 |
| hsa-mir-204 | chr9 | 72614710 | 72614820 | 44.63 | 28.57 | 38 |
| hsa-mir-33a | chr22 | 40626893 | 40626962 | 74.29 | 40 | 61.11 |
| hsa-mir-637 | chr19 | 3912411 | 3912510 | 77.97 | 34.29 | 44.44 |
| hsa-mir-648 | chr22 | 16843633 | 16843727 | 50.29 | 40 | 44.44 |
| hsa-mir-658 | chr22 | 36570224 | 36570324 | 61.86 | 40 | 44.44 |
| hsa-mir-659 | chr22 | 36573630 | 36573727 | 61.86 | 40 | 50 |

MIRNAS AS NOVEL THERAPEUTIC ADJUVANTS AND BIOMARKERS FOR THE PROGNOSIS AND TREATMENT OF DRUG RESISTANT BREAST CANCERS

CROSS REFERENCE TO RELATED APPLICATIONS

This application is a national phase application under 35 U.S.C. 371 of International Application No. PCT/US2013/070350, filed Nov. 15, 2013, which claims the benefit of priority of U.S. Provisional Patent Application No. 61/727,481 filed on Nov. 16, 2012. The entire contents of each of the above-referenced disclosures are hereby incorporated by reference.

BACKGROUND OF THE INVENTION

A. Field of the Invention

The invention relates to use of microRNA (miRNA) for treating cancer, as well as the use of these compositions to treat cancer.

B. Description of Related Art

Approximately 15-20% of all breast cancers are triple negative breast cancers (TNBCs). These cancers typically exhibit distinct, aggressive metastatic patterns. Prognoses for those receiving a TNBC diagnosis are often poor, and disproportionate numbers of breast cancer deaths follow. Despite better chemotherapy response rates in early-stages of TNBC disease, more than sixty percent of TNBC patients develop chemoresistance, which leads to early relapse and shortened survival.

miRNAs are small, non-protein encoding RNAs that function widely in gene regulation. Messenger RNAs of more than sixty percent of human protein-coding genes may be targeted by miRNAs, which are abundant in many human cell types (Friedman, et al., 2009). The human genome encodes over 1000 miRNAs (more than 1000 Homo sapiens miRNAs are listed in Manchester University's miRBase).

SUMMARY OF THE INVENTION

In one instance, there is disclosed a method for reducing growth of cancer cells, the method comprising administering an effective amount of a composition comprising hsa-miR-204 or a homolog thereof to a subject having or suspected of having cancer cells reduced or significantly reduced in expression of hsa-miR-204 or a homolog thereof. In certain aspects, brain-derived neurotrophic factor (BDNF) or ezrin is overexpressed or significantly overexpressed in the cancer cells of the subject having or suspected of having cancer cells reduced or significantly reduced in expression of hsa-miR-204 or a homolog thereof.

In some embodiments, the subject is a mammal. In certain aspects, the subject is a human. The subject may have cancer, such as a breast cancer, an ovarian cancer, or a pediatric renal tumor. In certain aspects, the breast cancer cells of the subject are triple negative breast cancer (TNBC) cells. In certain aspects, cancer cell growth is metastatic.

In some embodiments, the disclosed method for reducing growth of cancer cells further comprises determining the level of hsa-miR-204 or a homolog thereof in cells of the subject. In related embodiments, the disclosed method is for identifying a subject likely to benefit from therapy for reducing growth of cancer cells, the method comprising determining the level of hsa-miR-204 or a homolog thereof in cells of the subject.

In certain aspects, determining the level of hsa-miR-204 or a homolog thereof is by using a quantitative reverse transcription-polymerase chain reaction (qRT-PCR)-based method or an array hybridization-based method. In some aspects, determining the level of hsa-miR-204 or a homolog thereof is determining the level in a blood sample obtained from the subject of hsa-miR-204 or a homolog thereof. In some aspects, the level in a blood sample obtained from the subject of hsa-miR-204 or a homolog thereof is determined to be at a reduced level.

In some embodiments, the composition comprising hsa-miR-204 or a homolog thereof is formulated for systemic administration. In certain aspects, this composition is administered by intravenous injection. In certain further aspects, the composition comprising hsa-miR-204 or a homolog thereof further comprises a lipid-based delivery vehicle or a nanoparticle-based delivery vehicle.

In further embodiments, the subject is further administered a composition comprising a second active agent. In further aspects, the second active agent is a cytotoxic chemotherapeutic, a nanobioconjugate, or a miRNA other than hsa-miR-204 or a homolog thereof. In certain further aspects, the cytotoxic chemotherapeutic comprises a taxane, and in certain additional further aspects, the taxane is paclitaxel.

In some embodiments that include administration of a composition comprising a second active agent, the administration of a composition comprising hsa-miR-204 or a homolog thereof is at the same time as administration of the composition comprising the second active agent. In some additional embodiments, the administration of a composition comprising hsa-miR-204 or a homolog thereof is before or after administration of the composition comprising the second active agent. In certain aspects, the interval of time between administration of the composition comprising hsa-miR-204 or a homolog thereof and the second active agent may be 1 to 30 days, or it may be 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more hours or days, or any integer derivable therein.

In certain embodiments that also include administration of a composition comprising a second active agent, the administration of composition comprising the second active agent is administered before the composition comprising hsa-miR-204 or a homolog thereof. In certain further aspects that include this administration of a composition comprising a second active agent before the composition comprising hsa-miR-204 or a homolog thereof, cancer cells have become resistant to the second active agent. In certain additional further aspects, a composition comprising a second active agent is administered before the composition comprising hsa-miR-204 or a homolog thereof, and the second active agent is a chemostherapy drug. In certain additional further aspects, the second active agent is taxol. In certain additional further aspects, the second active agent is paclitaxel.

In some embodiments of the above-noted methods, the composition comprising hsa-miR-204 or a homolog thereof is taken from a preparation comprising a pharmaceutically acceptable carrier. In some aspects, the preparation further meets pharmacopeial requirements for sterility, pyrogens, and particulate matter or other contaminants, or is formulated for systemic administration, or both meets the above-noted pharmacopeial requirements and is formulated for systemic administration.

Further disclosed is a method for screening for potential sensitizer miRNA that, when inhibited, increases viability of cancer cell line cells cultured in a sub-lethal concentration of therapeutic active agent, the method comprising: culturing, for a period, cancer cell line cells in a miRNA-inhibitor-containing culture comprising a sub-lethal concentration of the therapeutic active agent together with an inhibitor of the candidate sensitizer miRNA; culturing, over the same period, cancer cell line cells in a miRNA-inhibitor-lacking culture comprising the sub-lethal concentration of the therapeutic active agent but lacking added inhibitor of the candidate sensitizer miRNA; and determining viability of the miRNA-inhibitor-containing cell population and the miRNA-inhibitor-lacking cell population after the period, wherein a candidate sensitizer miRNA is identified as a potential sensitizer miRNA if viability of the miRNA-inhibitor-containing cell population (cultured with therapeutic active agent and candidate sensitizer miRNA inhibitor) is higher or significantly higher than viability of the miRNA-inhibitor-lacking cell population (cultured with therapeutic active agent but lacking added inhibitor of the candidate sensitizer miRNA).

In certain aspects of this method for screening, the potential sensitizer miRNA is hsa-miR-204, hsa-miR-185, hsa-miR-211, hsa-miR-367-5p (also called hsa-miR-367*), or hsa-miR-133A, or a homolog of any one of these miRNAs. In certain aspects, the sub-lethal concentration of the therapeutic active agent is a concentration at which 80 percent of the cancer cell line cells remain viable after culture for 72 hours. In certain further aspects, the therapeutic active agent is taxol and/or other chemotherapy drugs, for example, at a sub-lethal concentration of 2 to 8 nM. In certain additional aspects, the cancer cell line cells are TNBC cells.

Further disclosed is a method for screening for potential de-sensitizer miRNA that, when inhibited, decreases viability of cancer cell line cells cultured in a sub-lethal concentration of therapeutic active agent, the method comprising: culturing, for a period, cancer cell line cells in a miRNA-inhibitor-containing culture comprising a sub-lethal concentration of the therapeutic active agent together with an inhibitor of the candidate de-sensitizer miRNA; culturing, over the same period, cancer cell line cells in a miRNA-inhibitor-lacking culture comprising the sub-lethal concentration of the therapeutic active agent but lacking added inhibitor of the candidate de-sensitizer miRNA; and determining viability of the miRNA-inhibitor-containing cell population and the miRNA-inhibitor-lacking cell population after the period, wherein a candidate de-sensitizer miRNA is identified as a potential de-sensitizer miRNA if viability of the miRNA-inhibitor-containing cell population (cultured with therapeutic active agent and candidate de-sensitizer miRNA inhibitor) is significantly lower than viability of the miRNA-inhibitor-lacking cell population (cultured with therapeutic active agent but lacking added inhibitor of the candidate de-sensitizer miRNA).

In certain aspects of this method for screening, the potential de-sensitizer miRNA is hsa-miR-129-3p, hsa-miR-296-5p, hsa-miR-216a, hsa-miR-1237, hsa-miR-1915*, hsa-miR-320d, or a homolog of any one of these miRNAs. In certain aspects, the sub-lethal concentration of the therapeutic active agent is a concentration at which 80 percent of the cancer cell line cells remain viable after culture for 72 hours. In certain further aspects, the therapeutic active agent is taxol and/or other chemotherapy drugs, for example, at a sub-lethal concentration of 2 to 8 nM. In certain additional aspects, the cancer cell line cells are TNBC cells.

In some embodiments, a method is disclosed for reducing growth of cancer cells comprising administering an effective amount of a composition comprising a sensitizer miRNA or a homolog of sensitizer miRNA to a subject having or suspected of having cancer cells reduced or significantly reduced in sensitizer miRNA expression. In some embodiments, a method is disclosed for reducing growth of cancer cells, the method comprising administering an effective amount of a composition comprising an inhibitor of a de-sensitizer miRNA or an inhibitor of a homolog of a de-sensitizer miRNA to a subject having or suspected of having cancer cells significantly increased in de-sensitizer miRNA expression.

In some embodiments, a method is disclosed for identifying a subject likely to benefit from therapy for reducing growth of cancer cells, the method comprising determining the level of a sensitizer miRNA or a homolog of sensitizer miRNA in cells of the subject. In certain aspects, the sensitizer miRNA of this method is hsa-miR-204, hsa-miR-185, hsa-miR-211, hsa-miR-367-5p (also called hsa-miR-367*), hsa-miR-133A, or a homolog of one of these sensitizer miRNAs.

In some embodiments, a method is disclosed for identifying a subject likely to benefit from therapy for reducing growth of cancer cells, the method comprising determining the level of a de-sensitizer miRNA or a homolog of de-sensitizer RNA in cells of the subject. In certain aspects, the de-sensitizer miRNA of this method is hsa-miR-129-3p, hsa-miR-296-5p, hsa-miR-216a, hsa-miR-1237, hsa-miR-1915*, hsa-miR-320d, or a homolog of one of these de-sensitizer miRNAs.

Sequences and SEQ ID NOs for stem loop sequences of sensitizer miRNAs hsa-miR-204, hsa-miR-185, hsa-miR-211, hsa-miR-367-5p (also called hsa-miR-367*), and hsa-miR-133A (i.e., for hsa-miR-133A-2), as well as for de-sensitizer miRNAs hsa-miR-129-3p (i.e., for −3p region of hsa-miR-129-1), hsa-miR-296-5p, hsa-miR-216a, hsa-miR-1237, hsa-miR-1915*, and hsa-miR-320d are provided in Table 1.

The term "homolog" when used in reference to a miRNA refers to a oligonucleotide that functions like the referenced miRNA, e.g., capable of targeting gene expression like the referenced miRNA. The homolog typically has the level of similarity in properties (e.g., sequence and structure) with the reference miRNA that would identify it to a person of ordinary skill in the art in view of this disclosure as being a homolog of the referenced sequence (e.g., using a miRNA homolog identification tool, such as miRNAminer under default/stringent parameters; see, e.g., miRNAminer tool available online at groups.csail.mit.edu/pag/mirnaminer/; see also Artzi, et al., 2008).

Unless otherwise specified (e.g., in reference to sequence homologies or alignments), percent values expressed herein for compounds are weight by weight and are in relation to the total composition.

The term "significantly" (e.g., when used in reference to, for example: "reduced" or "increased"; "lower" or "higher"; "repressed" or "overexpressed"; "fails to exceed" or "exceeds" or similar-type qualifiers) refers to a level in a referenced or test sample that is at least of a magnitude greater than the magnitude of the standard error of the assay used to assess the characteristic to which the qualifier applies. In some instances, statistical significance for the referenced or test sample may be associated with a P value of less than 0.25, 0.15, 0.10, 0.05, 0.025, 0.01, 0.005, 0.001, 0.0005, or 0.0001.

A pharmaceutically acceptable carrier may include, but is not limited to: a virus; a liposome; a nanoparticle; or a polymer, and any combination thereof. Related delivery vehicles may include, but are not limited to: liposomes, biocompatible polymers, including natural polymers and synthetic polymers; lipoproteins; polypeptides; polysaccharides; lipopolysaccharides; artificial viral envelopes; inorganic (including metal) particles; and bacteria, or viruses, such as baculovirus, adenovirus and retrovirus, bacteriophage, cosmid, or plasmid vectors.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. Similarly, the term "effective" means adequate to accomplish a desired, expected, or intended result.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. in relation to the total composition.

The compositions and methods for their use can "comprise," "consist essentially of," or "consist of" any of the ingredients or steps disclosed throughout the specification.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A. High resolution miRNA-CGH (comparative genomic hybridization) on selected pediatric renal tumors with (left) or without (right) miR-204 deletions. Deletion of genomic loci containing the miRNA is indicated by dotted perpendicular lines. Dots indicate position and value of each probe reflecting copy number change, represented in triplicate on the CGH array. The trend line represents the average value of the triplicate probe for each tumor. FIG. 1B. Graphs obtained from meta-analysis of high-resolution CGH of ovarian cancers (n=354; obtained from TCGA) representing a subset of cancers with or without deletion. The deletion of genomic loci containing hsa-miR-204 is indicated by dotted perpendicular lines. FIGS. 1C & D. Allelic PCR of hsa-miR-204 genomic locus in pediatric renal tumors (C) and ovarian cancers (D). The y-axis displays log 2 transformed relative quantification values. Dotted lines indicate the loss of copy threshold. FIGS. 1E-G. Graphical representation of qRT-PCR analysis showing levels of miR-204 in pediatric renal tumors (n=38; E), in advanced stage ovarian cancers (n=11; F) and, in breast cancers (n=10; G), when compared to normal matched control kidney (n=38), normal ovarian tissues (n=5) and normal matched breast tissues (n=10).

FIG. 2A. Hsa-miR-204 inhibits anchorage-independent growth. Graph depicts the number of colonies formed in soft agar wells by HEK-293 cells stably overexpressing either scramble or miR-204, further transfected with miR-204 inhibitor. (*) P<0.05; (**) P<0.01. Results are the average of three independent experiments. FIG. 2B. Hsa-miR-204 overexpression inhibits tumor growth. HEK-293 cells stably overexpressing either scramble control or hsa-miR-204. Bar graph representations correspond to mean tumor volume for hsa-miR-204 (n=9) and scramble control (n=9) transfectants. (*) P<0.001. FIG. 2C. Histological analysis of sections from tumor xenografts overexpressing either scramble (control) or hsa-miR-204 (miR-204). Images in the right panels represent magnified views of boxed regions indicated in the left panels. Tumor invasion in control transfectants is reflected by the invasion of tumor into renal tissue. FIG. 2D. Basement membrane matrix invasion assay of MDA-MB-231 cells transfected with 75 nM scrambled sequence (control) or hsa-miR-204 mimic (miR-204) or hsa-miR-204 mimic transfected cells further transfected with hsa-miR-204 inhibitor (miR-204+ inhibitor). Bar graph representations correspond to the average number of invaded cells counted microscopically in five different fields per filter. (***) P<0.001.

FIG. 3A. Representative lung sections with metastatic foci in neg. control groups. FIG. 3B. No hepatotoxicity in hsa-miR-204 injected mice. Sections of liver from hsa-miR-204 injected mice show no signs of hepatotoxicity.

FIGS. 4A-H. Hsa-miR-204 regulates expression of BDNF in cancers. FIGS. 4A-C. Higher BDNF expression correlates strongly with lower hsa-miR-204 expression in multiple cancers. Graphical representation of qRT-PCR analysis revealing an inverse correlation between hsa-miR-204 and BDNF expression in pediatric renal tumors (n=38; A), in advanced stage ovarian cancers (n=11; B), and in breast cancers (n=10; C), when compared to normal matched control kidney (n=38), normal ovarian tissues (n=5), and normal matched breast tissues (n=10). FIG. 4D. Schematic of the putative miR-204 binding sequence in the BDNF 3'-UTR. FIG. 4E. QRT-PCR analysis of hsa-miR-204 overexpressing cells and cells transfected with hsa-miR-204 inhibitors using BDNF specific primers. FIG. 4F. Western blot analysis of HEK-293 cells transfected with miR-204 mimic using anti-BDNF antibody (1:1000). β-actin was used as a loading control. Gel photographs are representative of three independent experiments. FIG. 4G. Graphical representation of band intensities quantified using the Total Labs TL100 1D gel analysis software (n=3). BDNF protein level for the control was set to 100.

FIG. 5A. Has-miR-204 suppresses activation of AKT and mTOR signaling. HEK-293 cells transfected with hsa-miR-204 were grown in serum-free conditions and subjected to western blot analysis using antiphospho-Ser$^{473}$-AKT (1:1000), anti-total-AKT (1:1000), anti-phospho-Ser$^{235/236}$-S6 (1:1000), antitotal-S6 (1:1000), anti-phospho-Thr$^{37/46}$-4E-BP1 (1:1000) and anti-total-4E-BP1 (1:1000). β-actin (1:10, 000) was used as a loading control. Gel photographs are representative of three independent experiments. FIG. 5B.

Hsa-miR-204 increases the sensitivity of HEK-293 cells to apoptosis as determined by Annexin V/PI staining using the FITC-Annexin V Apoptosis Detection Kit. The percentage cell population shown is the mean±SEM of three independent experiments. FIG. 5C. Western blot analysis of HEK-293 cells transfected with hsa-miR-204 using anti-caspase-3 (1:500) antibody and anti-PARP (1:1000) reveals increased cleavage of caspase-3 and PARP. β-actin (1:10,000) was used as a loading control. Gel photograph is representative of three independent experiments.

FIGS. 9A-B. Copy number loss of chromosomal regions containing miRNAs in tumors. FIG. 9A. Sample results for various human miRNAs and ovarian cancer, breast cancer, and pediatric renal tumors. FIG. 9B. Graphs obtained from meta-analysis of high-resolution CGH of breast cancers representing a subset of cancers with or without deletion. The deletion of genomic loci containing hsa-miR-204 is indicated by dotted perpendicular lines.

FIG. 10A. $\text{Log}_2$ fold change for more than 40 genes including BDNF. FIG. 10B. Down-regulated genes by biological functions. Note prevalence of BDNF among down-regulated genes in various categories of biological functions.

FIG. 11A. BDNF rescues hsa-miR-204-induced cell [non]migration phenotype. FIG. 11B. BDNF rescues hsa-miR-204-induced cell [non]invasion phenotype.

DESCRIPTION OF ILLUSTRATIVE EMBODIMENTS

Figure 1A:
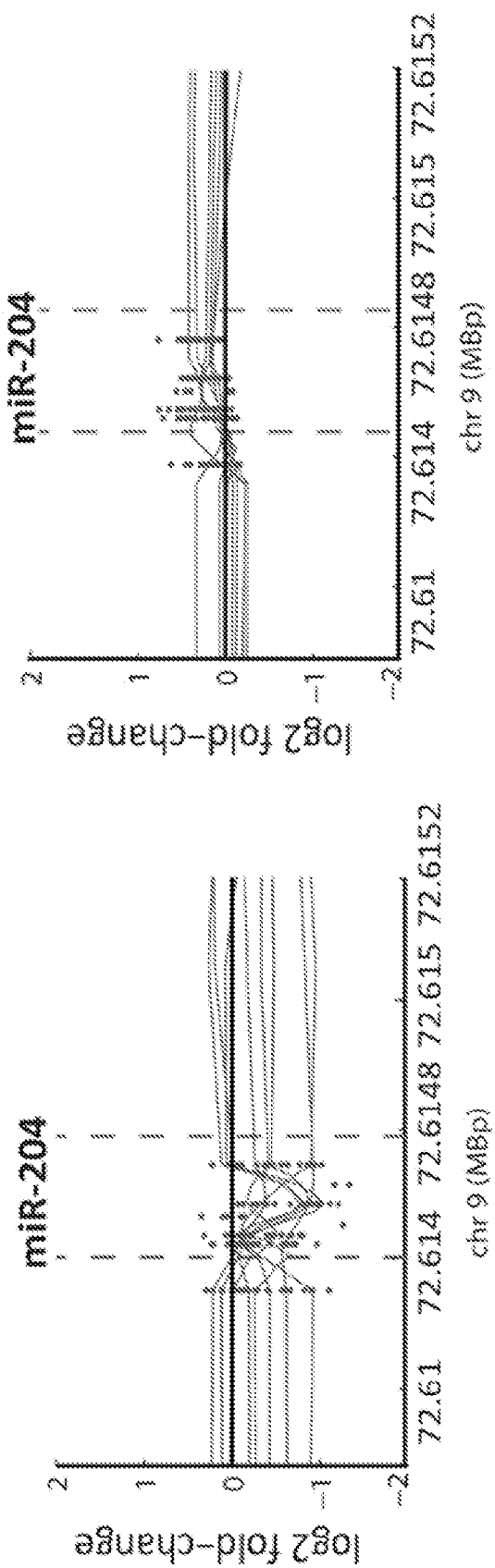
FIGS. 1A-1G. Genomic loss of miR-204 in cancers.
Figure 1B:
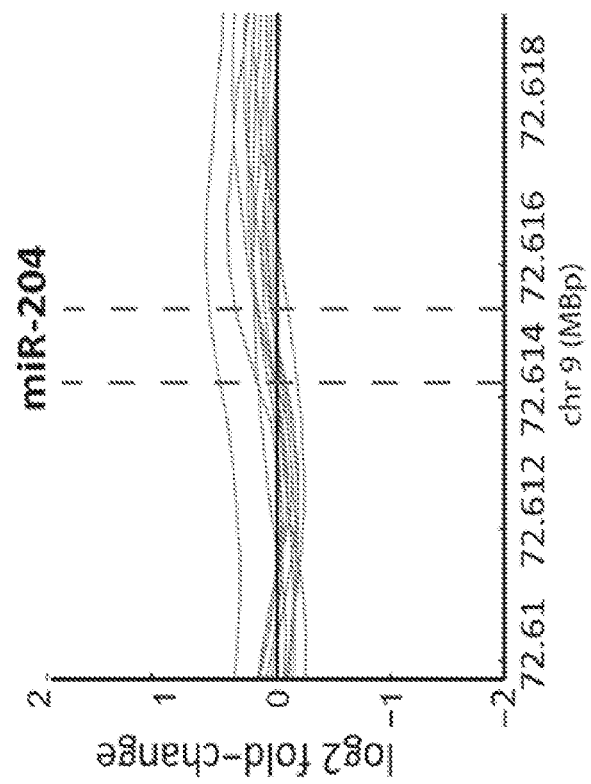
Figure 1B:
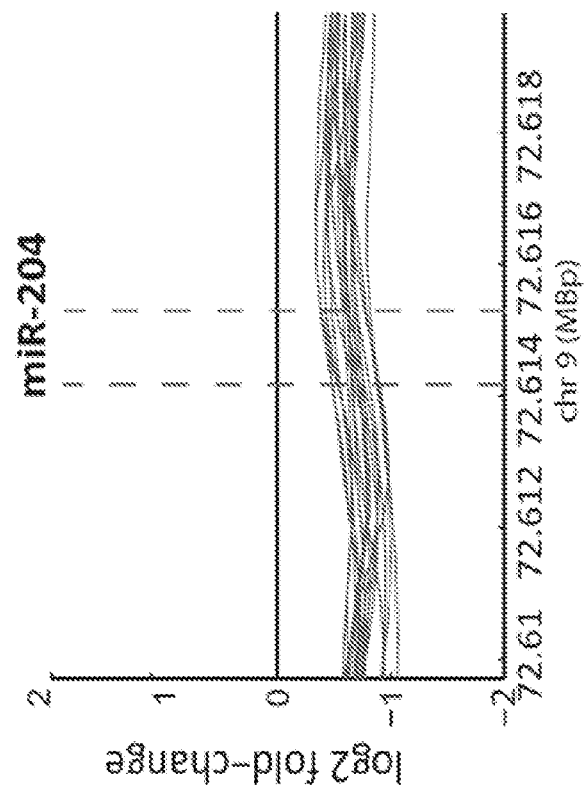

The inventors have demonstrated critical roles for miRNAs in mediating drug sensitivity/resistance in triple negative breast cancers (TNBCs) cells. Through high-throughput miRNA/miRNA-inhibitor library screens, the inventors have identified miRNAs that uniquely sensitize drug resistant TNBC cells to paclitaxel, a drug commonly used as a first line treatment for TNBC conditions. These screens also have revealed that miRNAs that sensitize resistant TNBC cells to paclitaxel may be present at a significantly lower levels in sera of relapsed metastatic TNBC patients compared to sera from healthy siblings.

In addition, candidate sensitizer miRNA has been shown to have drastically reduced expression in several cancers and to act as a potent tumor suppressor. Using liposome-based approaches, the inventors have shown in preclinical mouse tumor models that systemic delivery of candidate sensitizer miRNA suppresses breast cancer lung metastasis without hepatotoxicity.

The inventors have demonstrated that candidate sensitizer miRNA exerts its function by targeting genes involved in tumorigenesis. These include the gene encoding brain-derived neurotrophic factor (BDNF), a neurotrophin family member known to promote tumor angiogenesis and invasiveness. Analysis of primary tumors has revealed that a marked reduction in expression of candidate sensitizer miRNA is accompanied by increased expression of BDNF or its receptor tropomyosin-related kinase B (TrkB). These analyses also have revealed that loss of candidate sensitizer miRNA results not only in BDNF overexpression but also in both subsequent activation of the small GTPase Rac as well as actin reorganization through the AKT/mTOR signaling pathway leading to cancer cell migration and invasion.

Among some of the significant specific demonstrations of the inventors are the following: miRNA-mediated sensitization of drug resistant cancer cells by candidate sensitizer miRNA to paclitaxel; suppression of TNBC lung metastasis after systemic delivery of candidate sensitizer miRNA; and lower levels (potentially significant for diagnostic purposes) of candidate sensitizer miRNA in TNBC patient sera. Identification of miRNAs that confer drug sensitivity may help provide a new generation of therapeutics, as well as provide new prognostic tools to monitor TNBC treatment responses to specific drugs through analysis of miRNA expression profiles of TNBC cells. In addition, because paclitaxel is used in treating many types of cancer, the invention has beneficial implications not simply for breast cancer treatment but also for treatment of many other types of cancer.

The inventors have demonstrated that genomic loss of tumor suppressor hsa-miRNA-204 promotes cancer cell migration and invasion by activating AKT/mTOR/Rac1 signaling and actin reorganization.

Chromosomal regions containing microRNAs may be functionally important in cancers. The inventors have demonstrated that genomic loci encoding hsa-miR-204 are frequently lost in multiple cancers, including ovarian cancer, pediatric renal tumors, and breast cancers. In particular, hsa-miR-204 has been shown to have drastically reduced expression in several cancers and acts as a potent tumor suppressor, inhibiting tumor metastasis in vivo when systemically delivered.

The inventors have demonstrated that hsa-miR-204 exerts its function by targeting genes involved in tumorigenesis, including brain-derived neurotrophic factor (BDNF)—a neurotrophin family member which is known to promote tumor angiogenesis and invasiveness. Analysis of primary tumors further has revealed that increased expression of BDNF or its receptor tropomyosin-related kinase B (TrkB) parallel a markedly reduced expression of hsa-miR-204. Loss of hsa-miR-204 results in BDNF overexpression and subsequent activation of the small GTPase Rac as well as actin reorganization through the AKT/mTOR signaling pathway leading to cancer cell migration and invasion.

The microdeletion of genomic loci containing hsa-miR-204 is directly linked with the deregulation of key oncogenic pathways that provide crucial stimulus for tumor growth and metastasis. Accordingly, the inventors therapeutically manipulated hsa-miR-204 levels in order to suppress tumor metastasis.

Sequences for hsa-miR-204 and other miRNAs identified herein are provided in Table 1.

TABLE 1 miRBase Accession Nos., SEQ ID NOS., and Sequences of Select miRNAs: second- & fourth-row subsequences for each miRNA are -5p & -3p subsequences, respectively, where applicable.

| miRNA | miRBase MI000---- Acc. No. | SEQ ID NOS. | SEQUENCE |
|---|---|---|---|
| hsa-miR-204 | 0284 | 1 | GGCUACAGUCUUUCUUCAUGUGACUCGUGGAC |
|  |  | 2 | UUCCCUUUGUCAUCCUAUGCCU |
|  |  | 3 | GAGAAUAUAUGAAGGAG |
|  |  | 4 | GCUGGGAAGGCAAAGGGACGU |
|  |  | 5 | UCAAUUGUCAUCACUGGC |
| hsa-miR-185 | 0482 | 6 | AGGGGGCGAGGGAU |
|  |  | 7 | UGGAGAGAAAGGCAGUUCCUGA |
|  |  | 8 | UGGUCCCCUCCCC |
|  |  | 9 | AGGGGCUGGCUUUCCUCUGGUC |
|  |  | 10 | CUUCCCUCCCA |
| hsa-miR-211 | 0287 | 11 | UCACCUGGCCAUGUGACUUGUGGGC |
|  |  | 12 | UUCCCUUUGUCAUCCUUCGCCU |
|  |  | 13 | AGGGCUCUGAGCAGG |
|  |  | 14 | GCAGGGACAGCAAAGGGGUGC |
|  |  | 15 | UCAGUUGUCACUUCCCACAGCACGGAG |
| hsa-miR-367 | 0775 | 16 | CCAUU |
|  |  | 17 | ACUGUUGCUAAUAUGCAACUCU |
|  |  | 18 | GUUGAAUAUAAAUUGG |
|  |  | 19 | AAUUGCACUUUAGCAAUGGUGA |
|  |  | 20 | UGG |
| hsa-miR-133A-2 | 0451 | 21 | GGGAGCCAAAUGCUUUGCUAG |
|  |  | 22 | AGCUGGUAAAAUGGAACCAAAU |
|  |  | 23 | CGACUGUCCAAUGGA |
|  |  | 24 | UUUGGUCCCCUUCAACCAGCUG |
|  |  | 25 | UAGCUGUGCAUUGAUGGCGCCG |
| hsa-miR-129-1 | 0252 | 26 | GGAU |
|  |  | 27 | CUUUUUGCGGUCUGGGCUUGC |
|  |  | 28 | UGUUCCUCUCAACAGUAGUCAGG |
|  |  | 29 | AAGCCCUUACCCCAAAAAGUAU |
|  |  | 30 | CU |
| hsa-miR-296 | 0747 | 31 | AGGACCCUUCCAG |
|  |  | 32 | AGGGCCCCCCCUCAAUCCUGU |
|  |  | 33 | UGUGCCUAAUUCA |
|  |  | 34 | GAGGGUUGGGUGGAGGCUCUCC |
|  |  | 35 | UGAAGGGCUCU |
| hsa-miR-216a | 0292 | 36 | GAUGGCUGUGAGUUGGCU |
|  |  | 37 | UAAUCUCAGCUGGCAACUGUGA |
|  |  | 38 | GAUGUUC |
|  |  | 39 | UCACAGUGGUCUCUGGGAUUAU |
|  |  | -- | -- |
| hsa-miR-1237 | 6327 | 40 | GUGGGAGGGCCCAGGCGCGGGCAGGGGUGGGGGUGGCAGAGCGCUGUCC |
|  |  | 41 | CGGGGGCGGGGCCGAAGCGCG |
|  |  | 42 | GCGACCGUAAC |
|  |  | 43 | UCCUUCUGCUCCGUCCCCAG |
|  |  | -- | -- |
| hsa-miR-1915* | 8336 | 44 | UGAGAGGCCGC |
|  |  | 45 | ACCUUGCCUUGCUGCCCGGGCC |
|  |  | 46 | GUGCACCCGUGGG |
|  |  | 47 | CCCCAGGGCGACGCGGCGGG |
|  |  | 48 | GGCGGCCCUAGCGA |
| hsa-miR-320d-1 | 8190 | 49 | UUCUCGUCCCAGUUCUUCCCAAAGUUGAG |
|  |  | 50 | AAAAGCUGGGUUGAGAGGA |
|  |  | -- | -- |
|  |  | -- | -- |
|  |  | -- | -- |

A. MicroRNAs and Cancer.

Identification of chromosomal regions harboring oncogenes and tumor suppressor genes has led to better understanding of the tumor pathogenesis and better treatment outcomes (Bayani, et al., 2007). Although several cancer-related genes have been identified in regions with chromosomal abnormalities (Albertson, et al., 2003), additional regions with random or recurrent chromosomal abnormalities harboring factors important in cancer growth and progression remain to be identified. Recent studies have indicated that microRNAs (miRNAs) are one such group of factors (Varambally, et al., 2008). MiRNAs are small, endogenous, non-coding RNAs that regulate post-transcriptional gene expression by binding to 3' untranslated (UTR) regions of target mRNAs. MiRNAs are known to have important functions in multiple biological processes including development and differentiation (Bartel, et al., 2004). Deregulated expression of miRNAs has been implicated in several human diseases including cancer (Bartels, et al., 2009). Evidence suggests that miRNAs can act as oncogenes or tumor suppressor genes (Esquela-Kerscher, et al., 2006).

Hsa-miR-204 has been identified as often being lost in multiple cancers. Results of studies by the inventors have demonstrated that hsa-miR-204 acts as a potent tumor suppressor by suppressing the function of genes associated with tumorigenesis, including brain-derived neurotrophic factor (BDNF). BDNF is a physiologically important nerve growth factor that plays a critical role in the development of nervous system by binding and subsequently activating the tyrosine kinase receptor, tropomyosin-related kinase B (TrkB) (Lewin, 1996; Segal, et al., 1996). In addition, BDNF/TrkB pathway is reported to have a critical role in tumorigenesis as it promotes proliferation, differentiation, angiogenesis and tumor invasiveness (Au, et al., 2009). Overexpression of BDNF/TrkB has also been implicated in poor prognosis of several solid tumors including neuroblastoma, ovarian, breast, prostate and lung cancers (Brodeur, 2003; Edsjo, et al., 2003; Nakagawara, et al., 1994). Loss of hsa-miR-204 results in BDNF/TrkB overexpression and concomitant activation of AKT/mTOR/Rac1 signaling pathway leading to actin reorganization during cancer cell migration and invasion. These results underline that chromosomal regions containing specific miRNAs may have particular functional importance in tumorigenesis.

B. Somatic Loss of Hsa-miR-204 in Cancers.

Figure 1C:
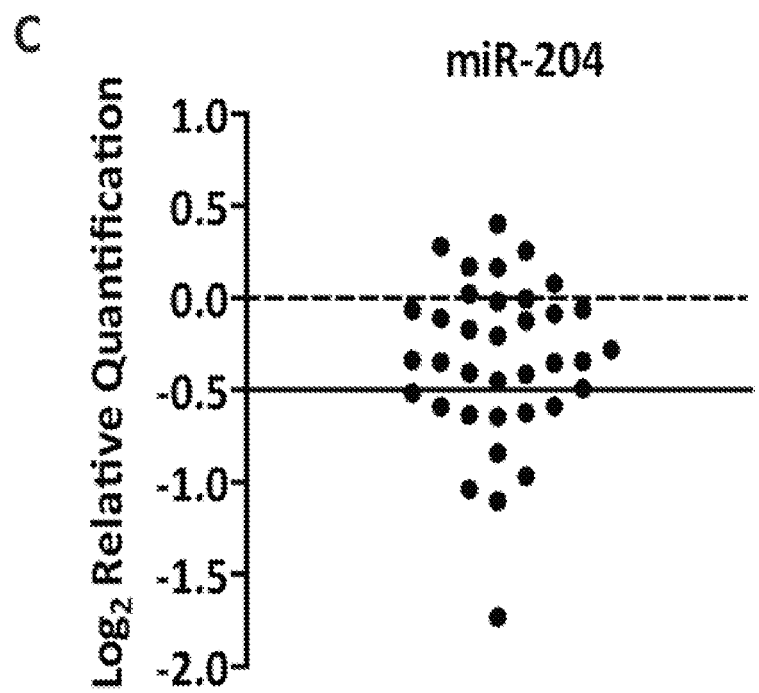
Figure 1D:
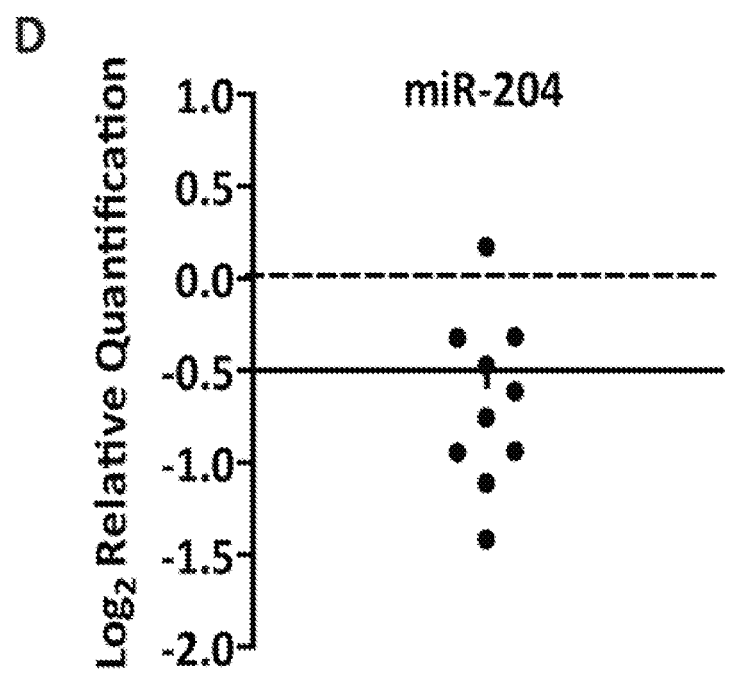
Figures 1E, 1F, 1G:
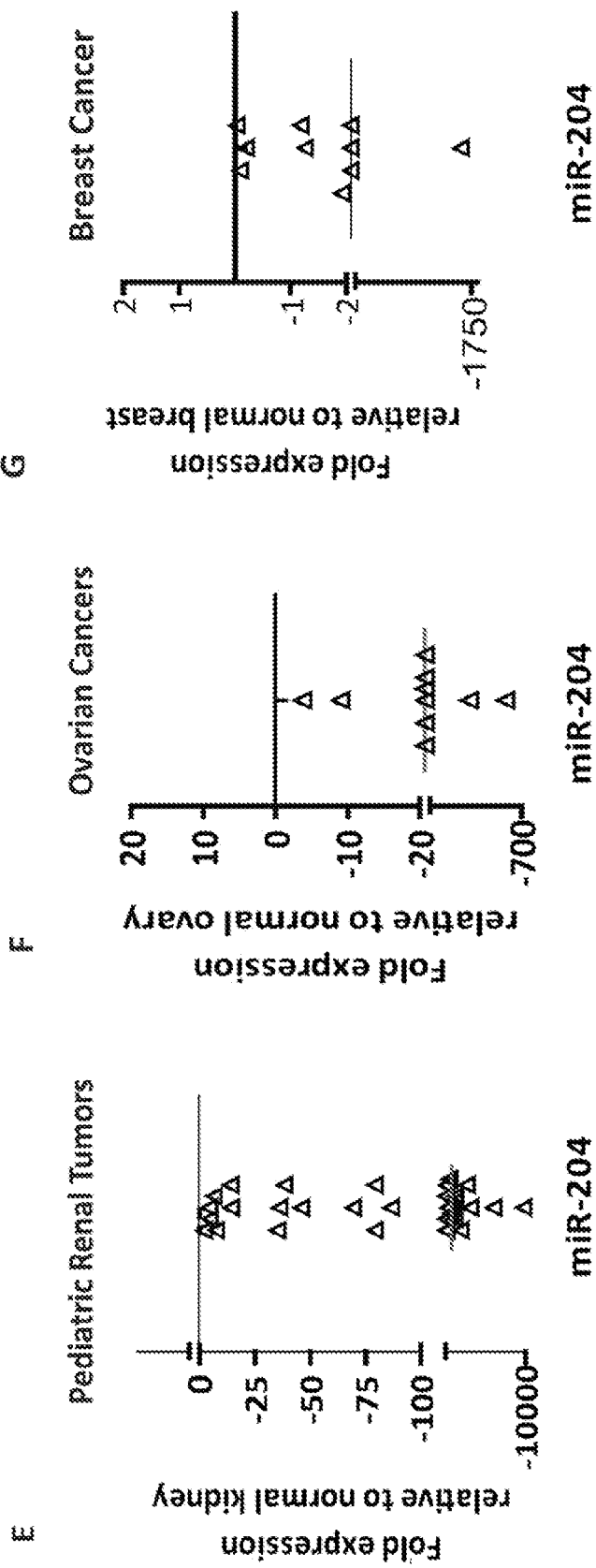
Figure 9B:
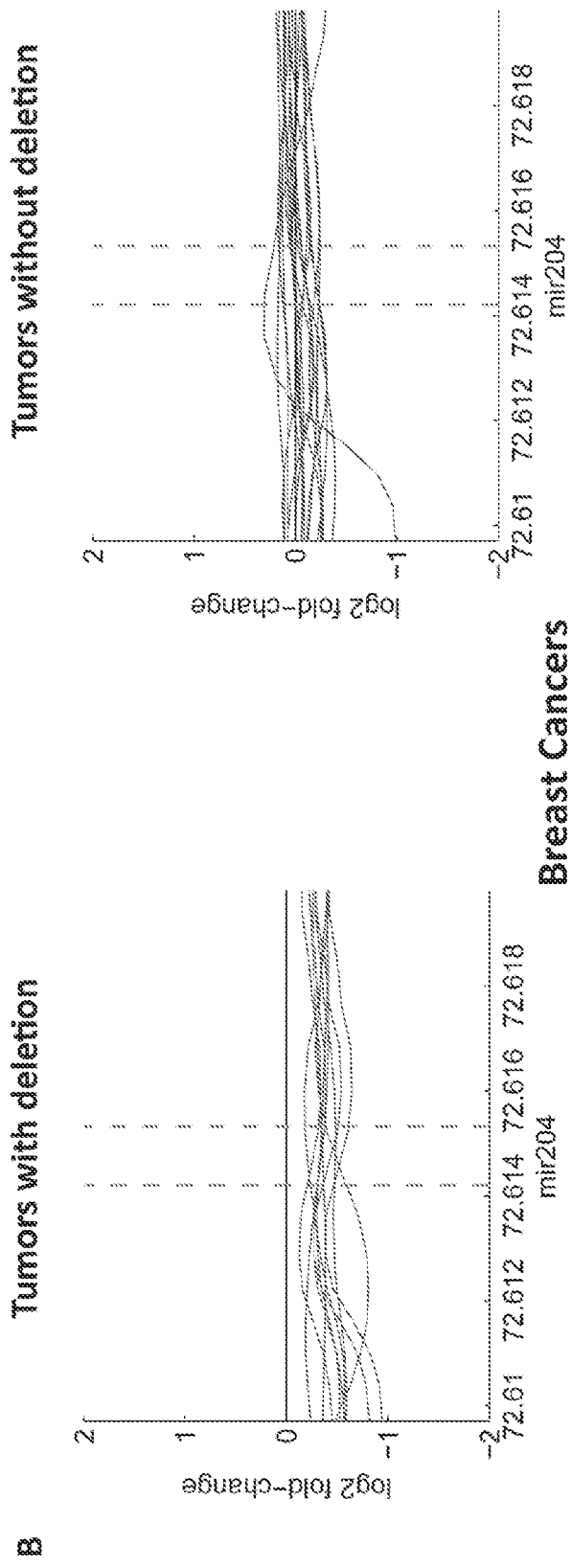

To identify miRNAs that are associated with aberrant chromosomal regions in human cancers, high-resolution custom miRNA comparative genomic hybridization (CGH) was used together with high density CGH public domain datasets for ovarian cancers, breast cancers and pediatric renal tumors. This analysis revealed several miRNAs in the minimal chromosomal deletion and amplification regions of these tumors. To begin to understand the functional importance of chromosomal loci associated with miRNAs in tumorigenesis, miRNAs exhibiting genomic loss were examined (FIG. 1 and, for example, FIG. 9A). The 9q21.12 chromosomal region containing hsa-miR-204 was frequently lost in 44.63% (158/354) of ovarian cancers, 28% (10/35) of breast cancers, and 40% (15/38) of pediatric renal tumors (concerning pediatric renal tumors and ovarian cancers, see also respectively FIGS. 1A and 1B; for breast cancers, see FIG. 9B), which is further verified by quantitative genomic real-time PCR analysis (FIGS. 1C and 1D). Furthermore, reduction in the levels of mature miR-204 also strongly correlated with its genomic DNA content in all three tumor types (FIGS. 1E, 1F and 1G).

C. Hsa-miR-204 Acts as a Potent Tumor Growth and Metastasis Suppressor.

Figure 2A:
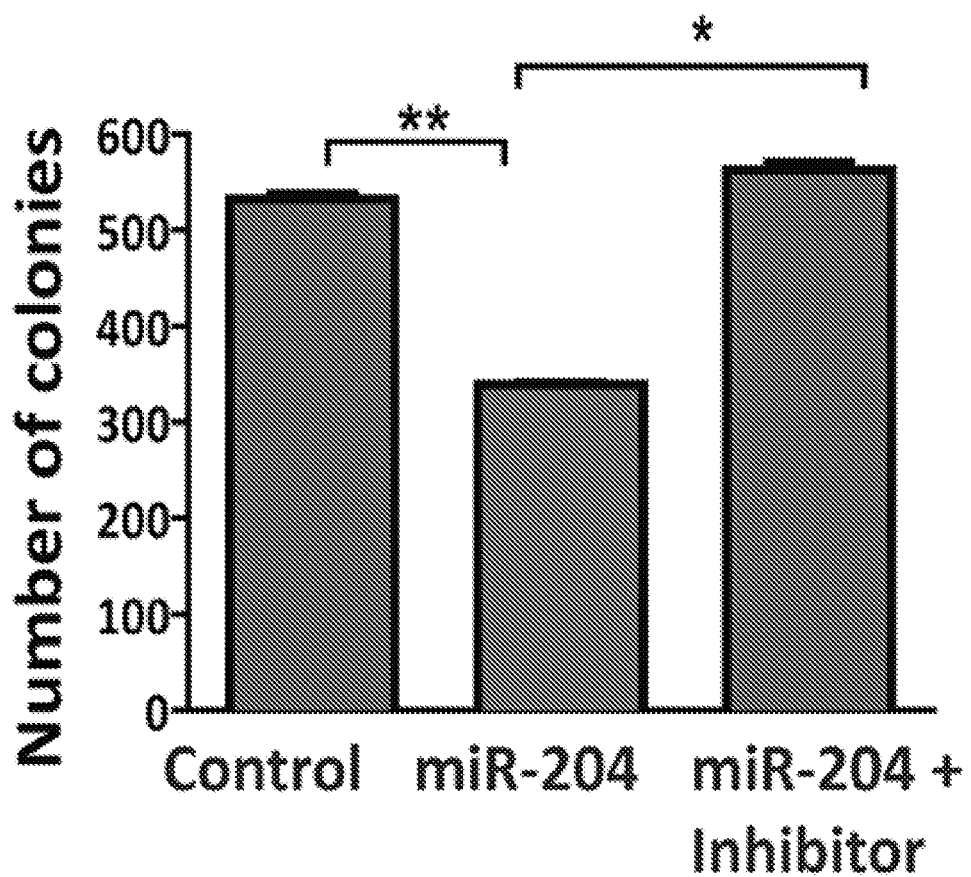
FIGS. 2A-D. Hsa-miR-204 inhibits tumor growth and metastasis.
Figure 2B:
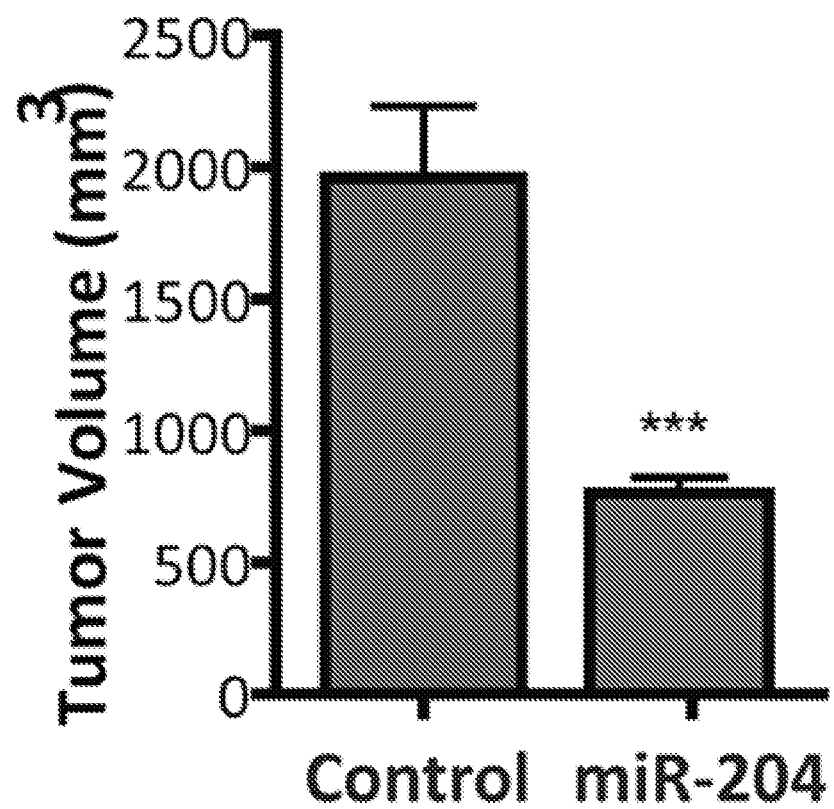
Figure 2C:
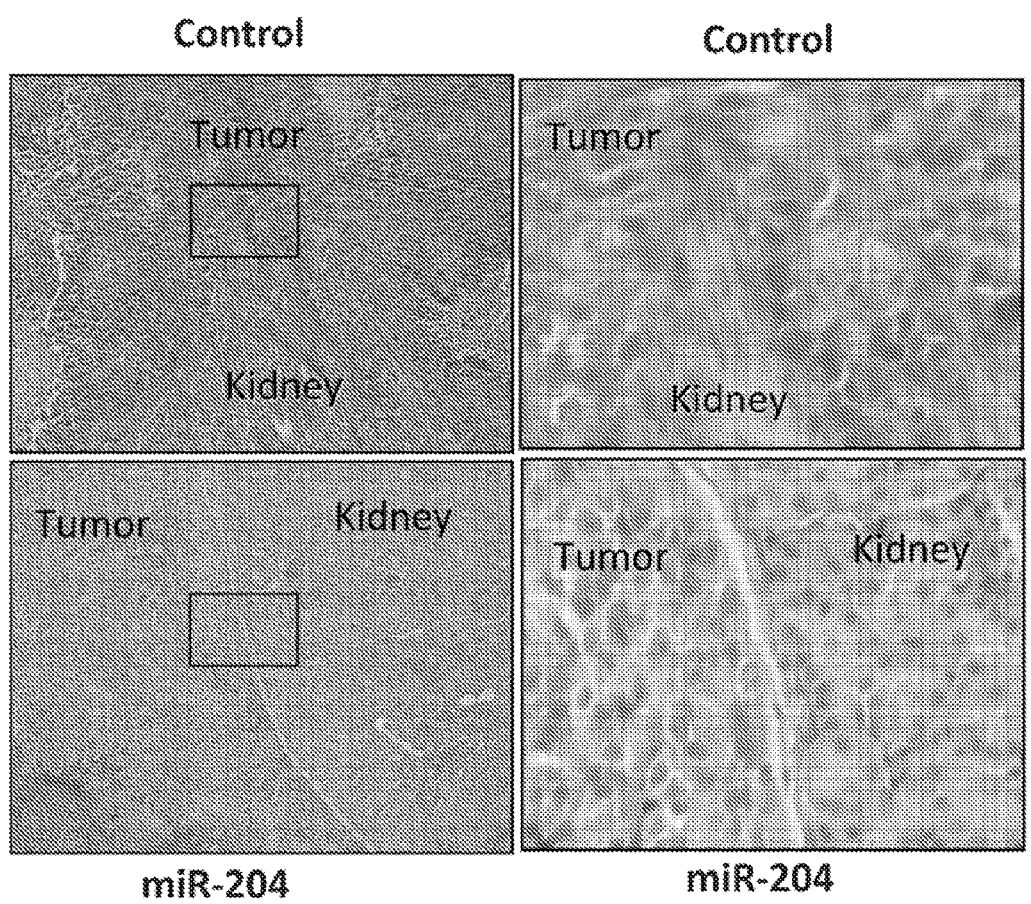
Figure 2D:
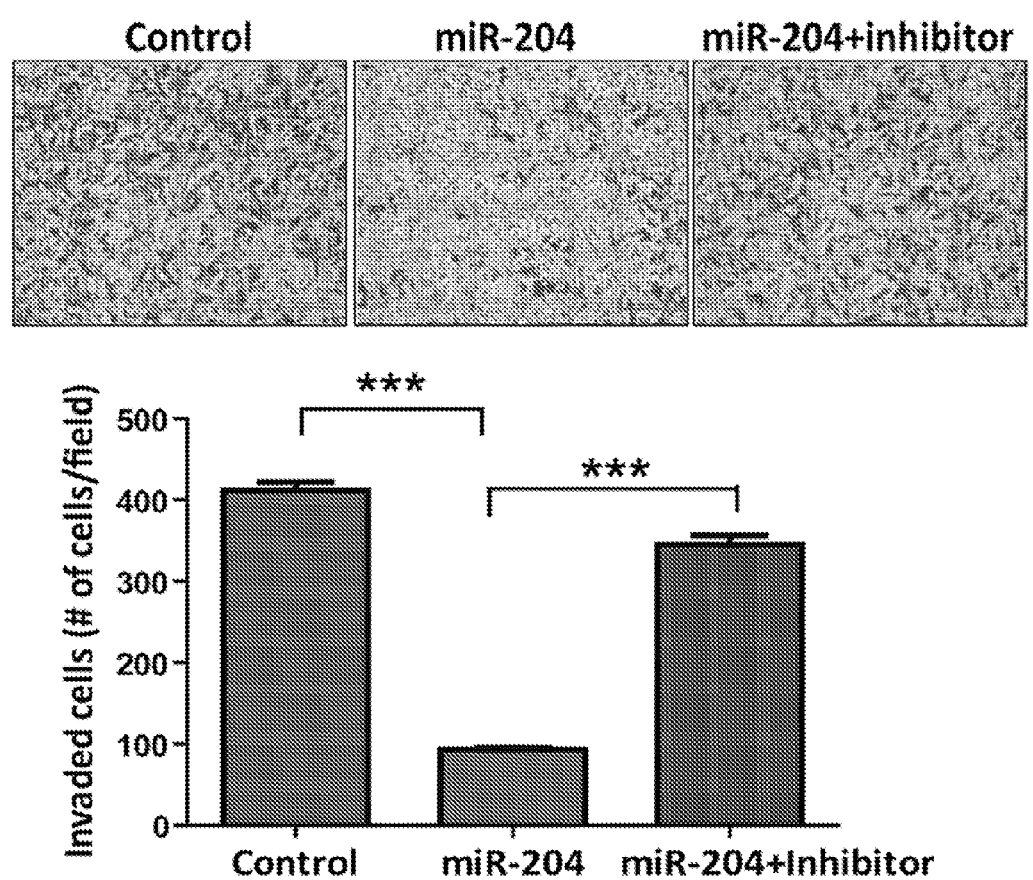

The drastically reduced expression of hsa-miR-204 in multiple cancer tissues prompted addressing the role of hsa-miR-204 in tumorigenesis. The effect of hsa-miR-204 on anchorage independent growth was first addressed. HEK-293 cells passaged over 52 times are reported to be highly tumorigenic (Shen, et al., 2008), and embryonal kidney HEK-293 cells overexpressing hsa-miR-204 exhibited reduced colony-forming capacity. But colony-forming capacity was rescued with the overexpression of an inhibitor of hsa-miR-204 (FIG. 2A). Similar results were also obtained with hsa-miR-204 overexpression in breast cancer MDA-MB-231 cells and ovarian cancer SKOV3 cells (data not shown). Further to confirm the potential tumor suppressor-like activity of hsa-miR-204, high-passage HEK-293 cells stably overexpressing either hsa-miR-204 or a scrambled sequence were injected into the kidney capsules of nude mice and tumor growth and metastasis were evaluated 24 days after injection. In sharp contrast to control tumors, hsa-miR-204 overexpressing tumors were dramatically reduced in size. Whether hsa-miR-204 also inhibits tumor cell invasion was next examined. Histological analysis of xenograft tumor sections indicated drastically decreased or no invasiveness of tumors into renal tissues that overexpressed miR-204 compared to control (FIG. 2C). Consistent with this, hsa-miR-204 overexpression drastically reduced the migratory and invasive capabilities of breast cancer (MDA-MB-231) and ovarian cancer (SKOV3) cells in vitro (FIG. 2D; and data not shown).

D. Therapeutic Targeting of Hsa-miR-204.

Figure 3A:
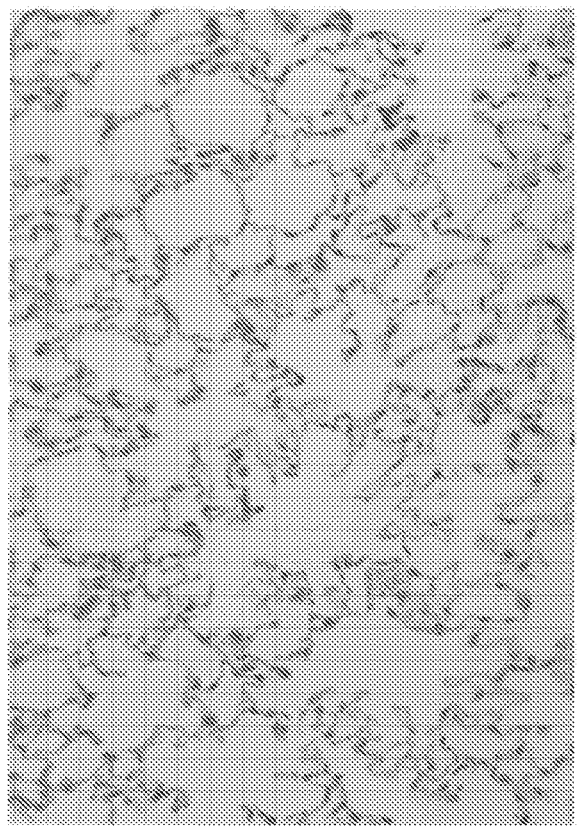
FIGS. 3A-3B. Systemic delivery of miR-204 suppresses tumor metastasis.
Figure 3A:
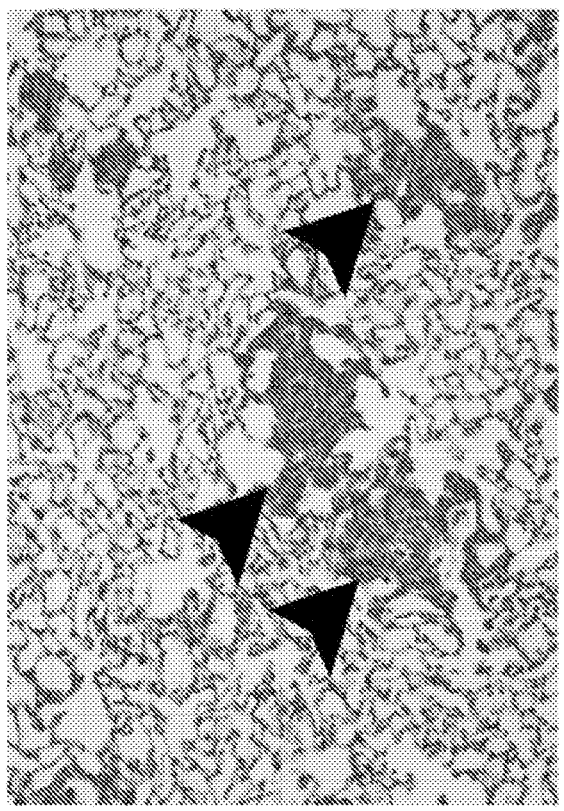
Figure 3B:
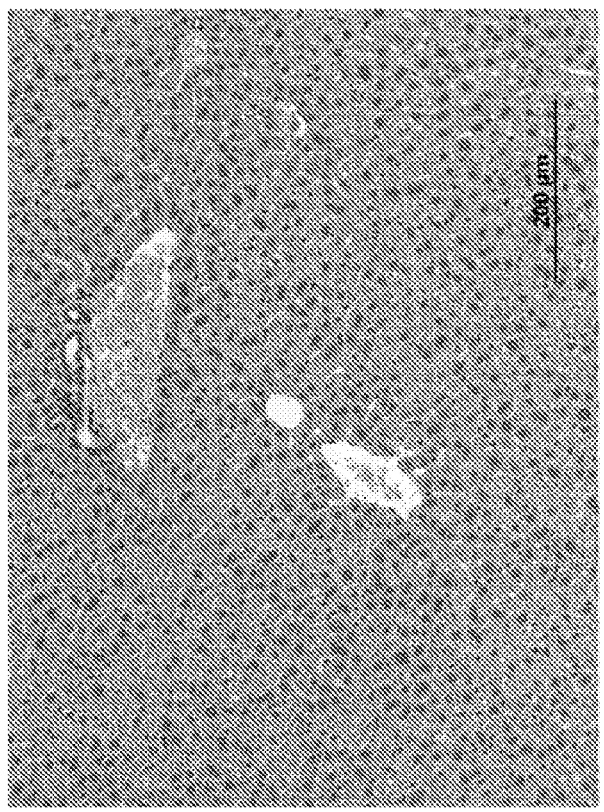
Figure 3B:

To further substantiate the metastasis suppressor activity of hsa-miR-204, therapeutic experiments in a breast cancer-lung metastasis model were performed. Lung metastases were first established by tail vein injection of MDA-MB-231 breast cancer cells expressing luciferase-GFP. Subsequently, hsa-miR-204 or hsa-miR-204 mutant oligo (negative control) were injected into the tail vein of these nude mice every five days for 30 days using a LANCErII lipid-based in vivo delivery vehicle. Interestingly, systemic delivery of hsa-miR-204 resulted in significant reduction or elimination of lung metastases, while, in contrast, hsa-miR-204 mutant oligo injected mice had metastasis including severe lung metastasis (FIG. 3A). In particular, mice injected with hsa-miR-204 displayed no obvious side effects at least as revealed by the absence of hepatotoxicity or a change in the body weight (FIG. 3B; and data not shown). These results indicate that hsa-miR204 and its homologs can form the basis for safe and viable therapeutic regimens to treat tumor growth and metastasis.

In similar experiments, mice were transplanted with triple negative breast cancer cells and two groups of mice were injected via tail vein either with miR-204 oligos or oligos with seed sequence mutated. Tail vein injection were given every 6 days for 30-days. Interestingly, systemic delivery of miR-2×4 resulted in significant reduction or elimination of lung metastases, while miR-2×4 mutant oligo injected mice had severe lung metastasis. These results indicate that miR-204 can be therapeutically targeted to treat tumor growth and metastasis

E. Hsa-miR-204 Targets Genes Associated with Tumorigenesis.

Figure 10A:
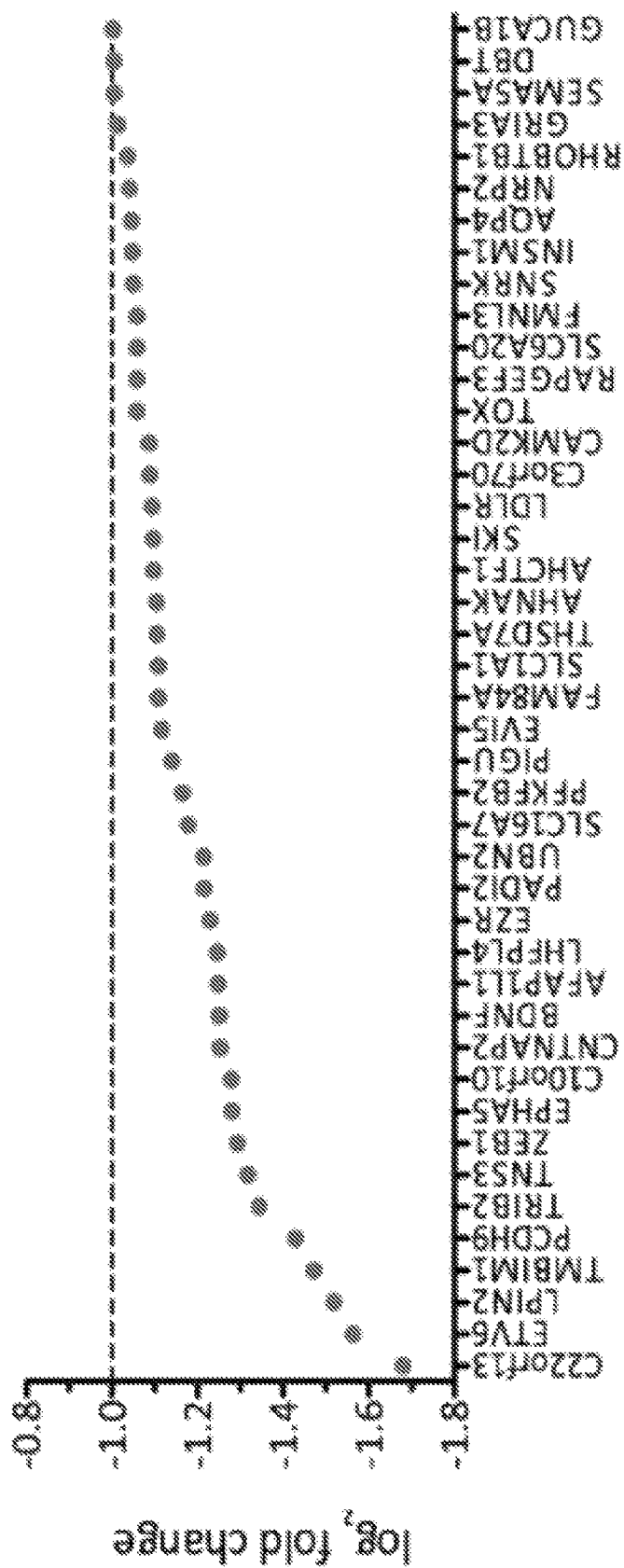
FIGS. 10A-B. Hsa-miR-204 targets genes associated with tumorigenesis.
Figure 10B:
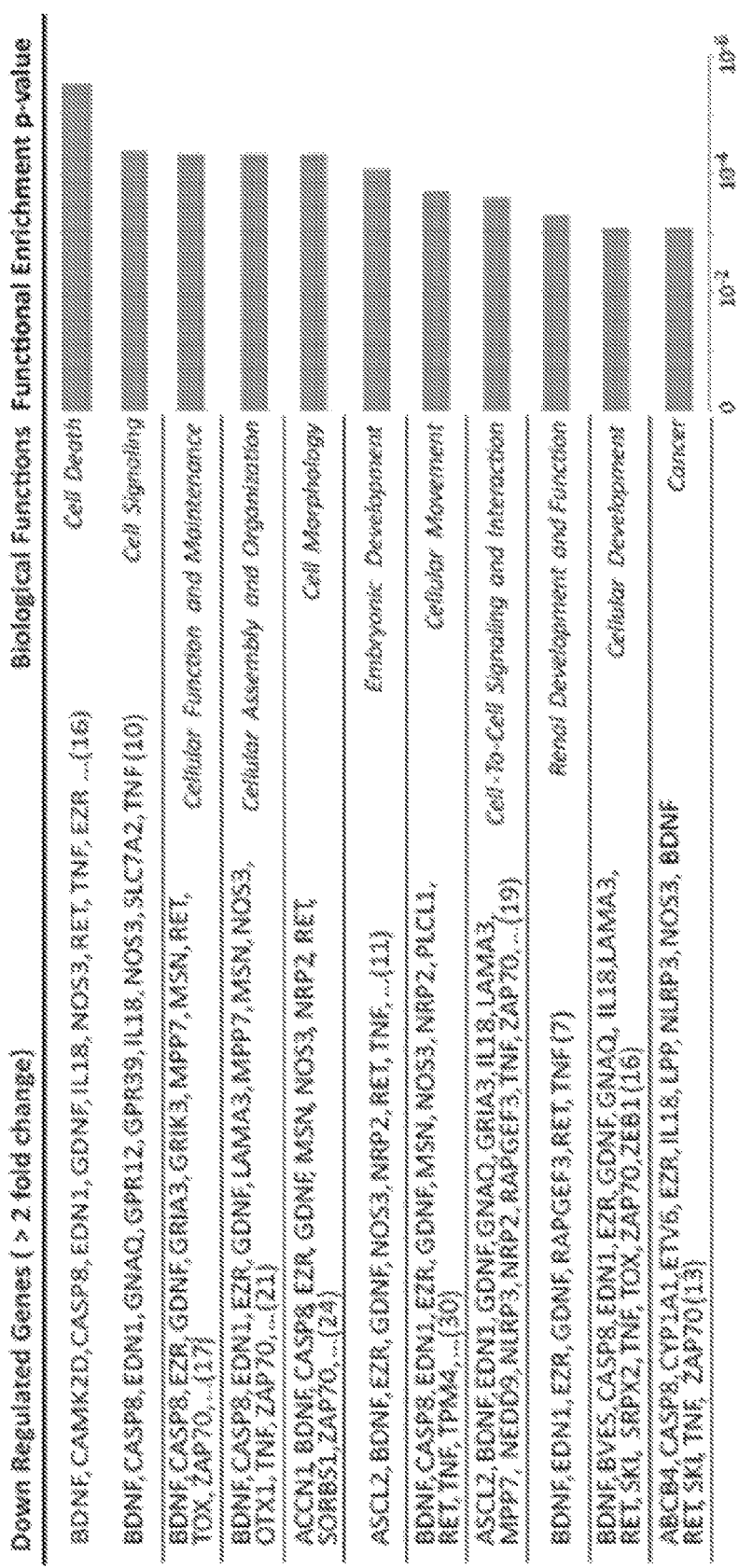

To understand the mechanism undergirding the role of hsa-miR-204 may play in tumorigenesis, genes regulated by miR-204 were identified. Because most miRNAs act to decrease target mRNA levels (Guo, et al., 2010), gene expression analyses on cells overexpressing hsa-miR-204 were performed and potential targets of hsa-miR-204 were determined. Of the genes altered in hsa-miR-204 overexpressing cells, downregulated genes are likely to be directly targeted by hsa-miR-204. Interestingly, several of the downregulated genes are associated with cancer-related processes and physically or functionally interact with each other, as revealed by pathway-based analyses (FIGS. 10A and 10B). Of these genes, detailed analyses were performed on one such gene: BDNF, which showed higher levels of alteration in microarray analysis and was featured in all predicted biological pathways with highest functional enrichment significance. BDNF, with its receptor TrkB, is known play a critical role in tumor angiogenesis and metastasis (Edsjo, et al., 2003; Nakagawara, et al., 1994). Moreover, multiple target prediction algorithms, including Sv/MicrO (Liu, et al., 2010), Bayesian decision fusion approach (Yue, et al., 2010) and miRmate (Du, et al., 2009) that the inventors generated, as well as TargetScan (Lewis, et al., 2005) and Pictar (Krek, et al., 2005), also predicted BDNF to be targeted by hsa-miR-204. Furthermore, the hsa-miR-204 binding site was found to be evolutionarily conserved throughout vertebrates, suggesting that it has an important regulatory function across a variety of species. Importantly, hsa-miR-204 and BDNF/TrkB expression showed a strong inverse correlation in several tumors (FIGS. 4A, 4B, and 4C).

Figure 4D:
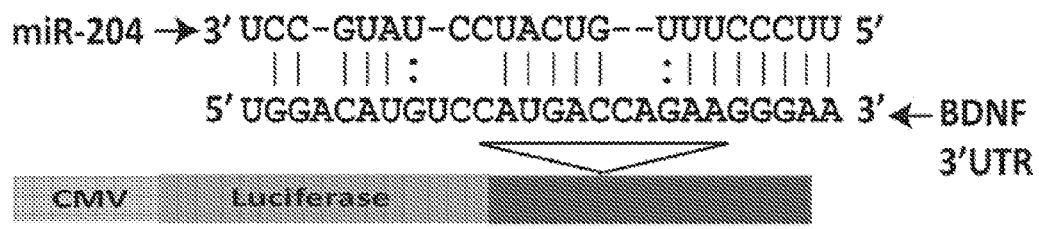

To validate microarray and target prediction results, whether hsa-miR-204 targets BDNF by binding to the predicted site in its 3' UTR was first investigated (FIG. 4 D). Indeed, luciferase activity of a pMIR-reporter construct containing the BDNF 3'-UTR was significantly repressed, which was further reduced in cells overexpressing hsa-miR-204 when compared to the construct without the 3'-UTR. In contrast, mutation of the seed sequence in the BDNF 3'-UTR-containing construct not only restored luciferase activity to near that of the wildtype construct but also rendered transcripts from the mutant construct insensitive to hsa-miR-204 overexpression, confirming a specific interaction between hsa-miR-204 and the predicted binding site in the BDNF 3'-UTR.

Figures 4E, 4F:
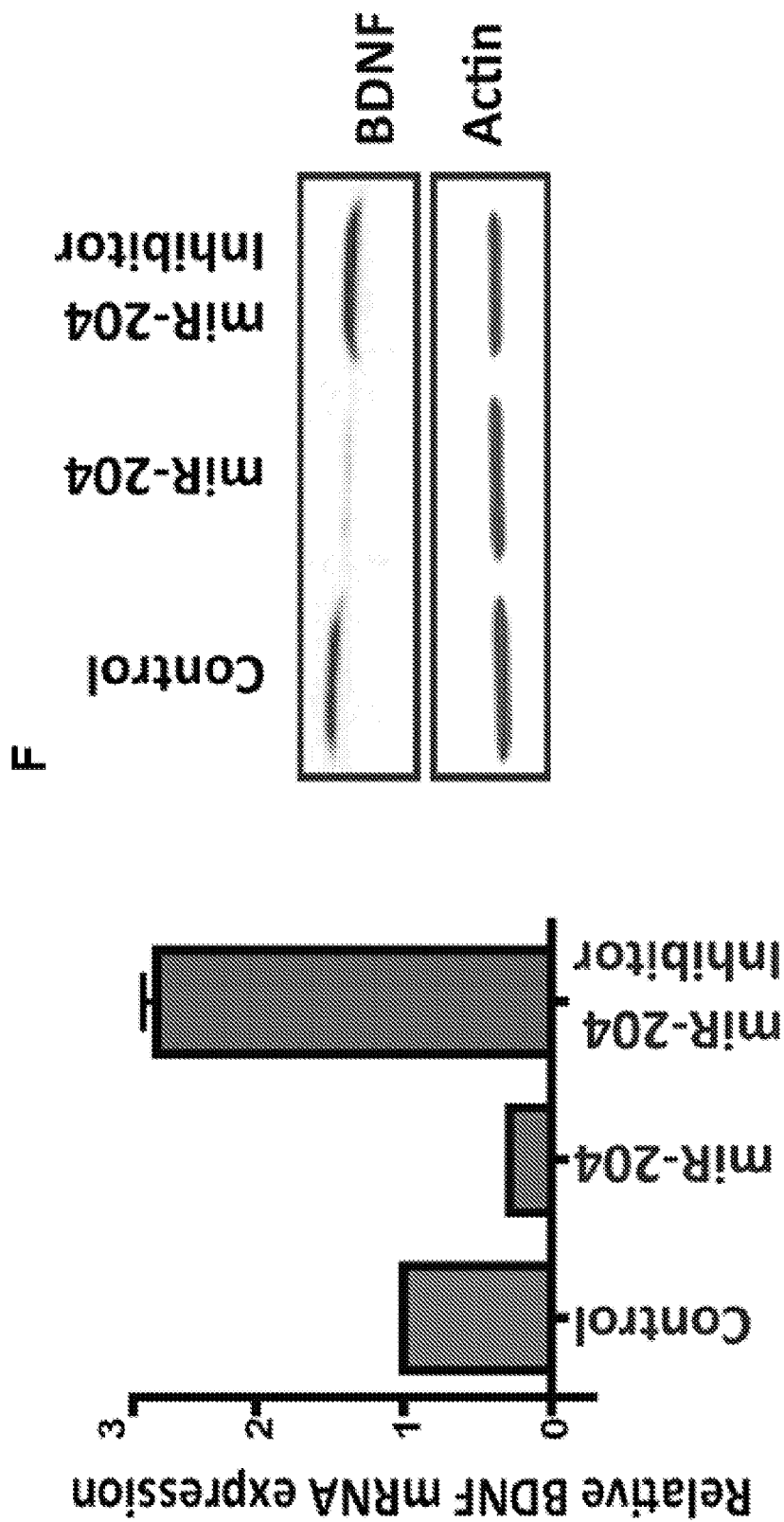
Figure 4G:
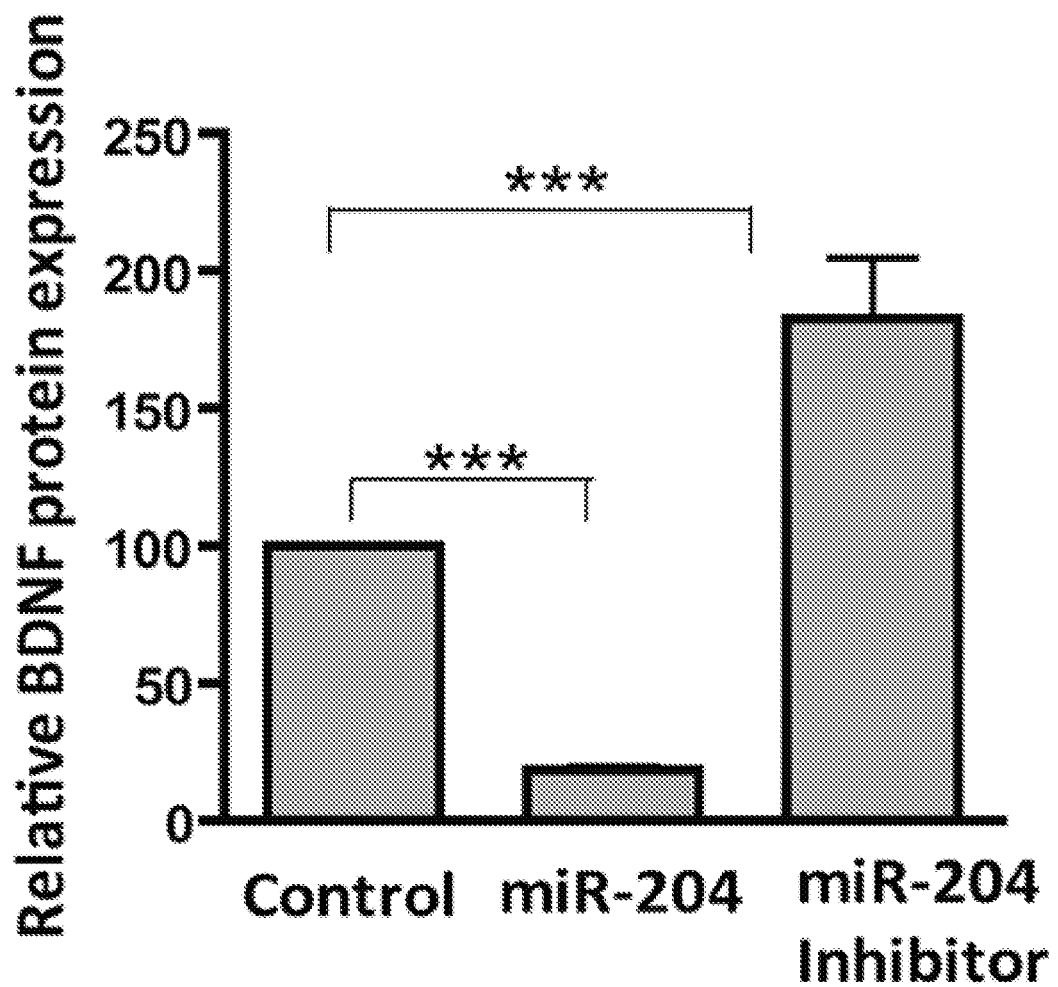
Figure 11A:
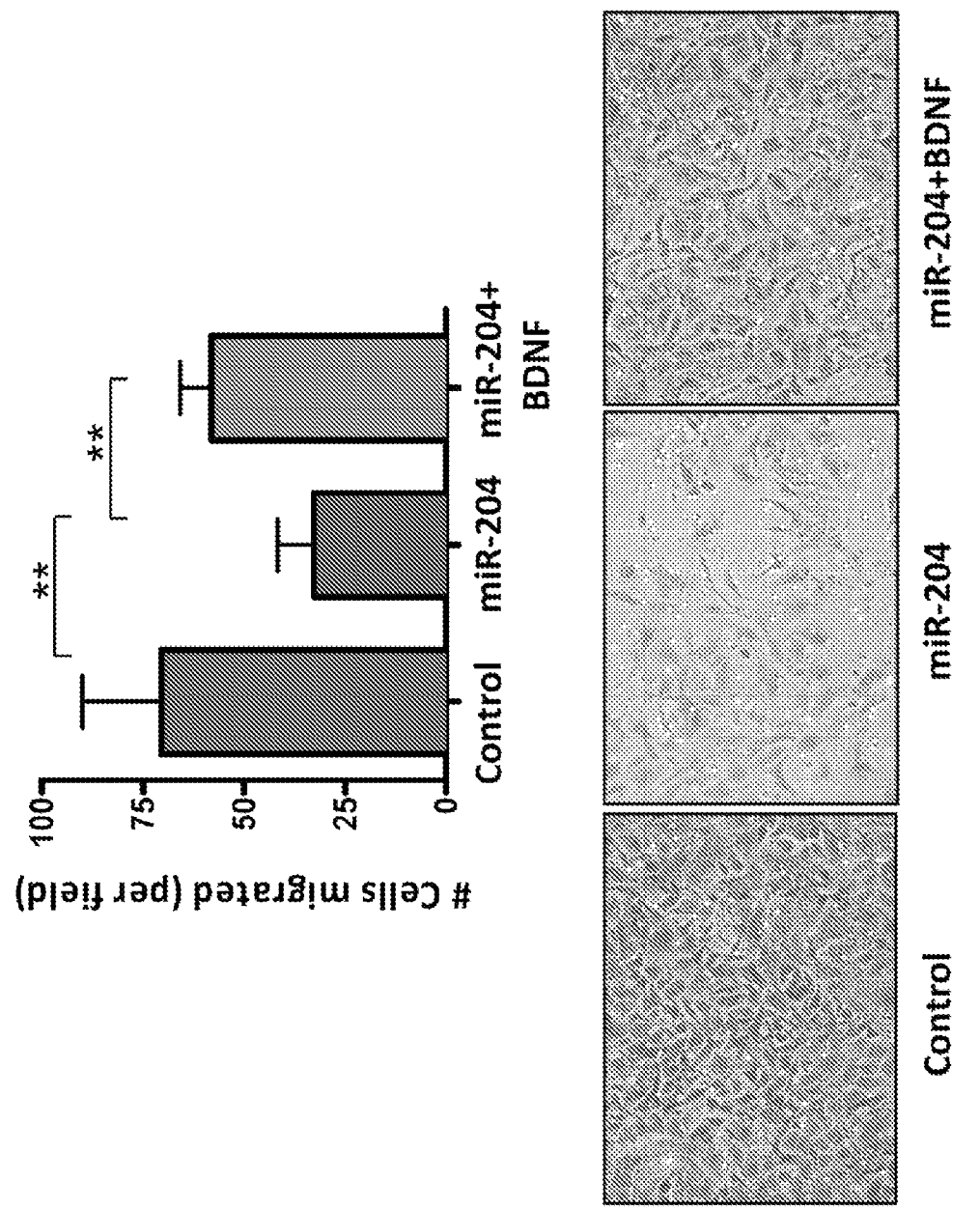
FIGS. 11A-B. BDNF rescues hsa-miR-204-associated or -induced phenotypes.
Figure 11B:
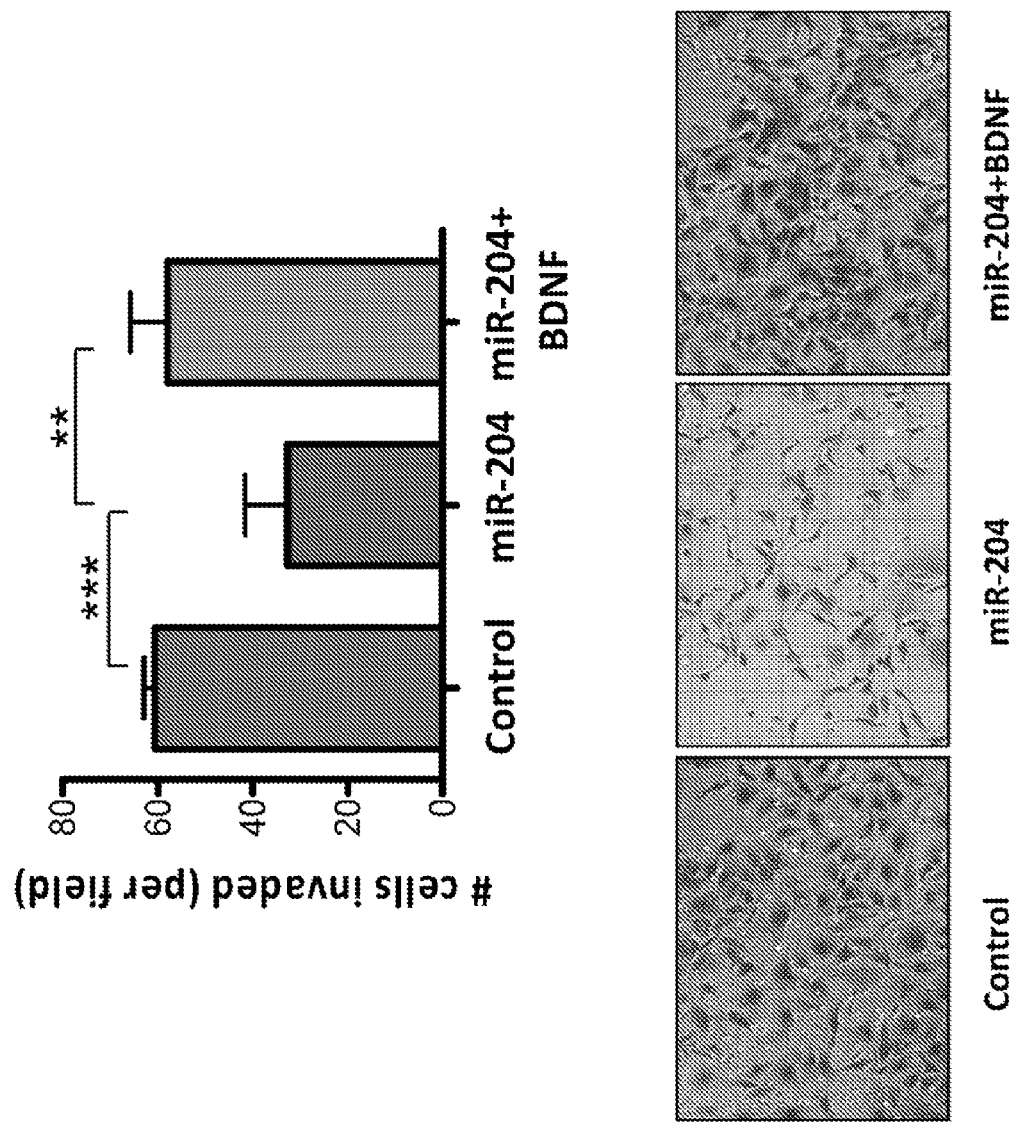

To further substantiate these results, the levels of BDNF in cells overexpressing hsa-miR-204 were determined. MiR-204 overexpression resulted in significant reduction of BDNF both at the RNA and protein levels (FIGS. 4E, 4F, and 4G). Next, whether or not BDNF is a functionally important target of miR-204 was examined. To address this, rescue experiments were performed. Reintroduction of BDNF rescued hsa-miR-204 induced phenotypes including anchorage-independent growth, cell migration and invasion (FIGS. 11A & 11B; and data not shown). These results suggest that hsa-miR-204-meditated regulation of BDNF is an important event in cancer cell growth, migration, and invasion.

F. Loss of Hsa-miR-204 Activates AKT/mTOR Signaling and Rac1 Translocation in Cancer Cells.

Figure 5A:
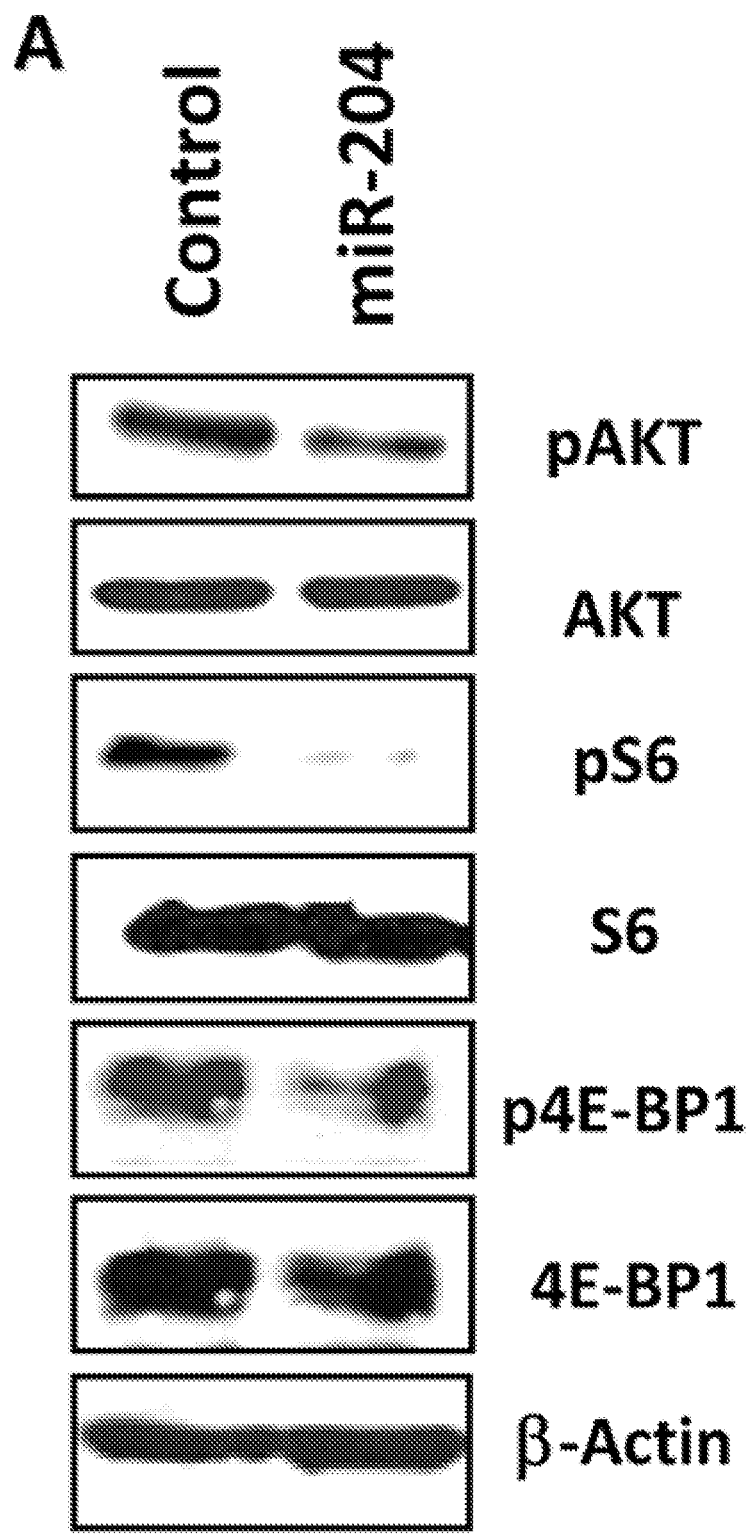
FIGS. 5A-C. Hsa-miR-204 inhibits tumor cell migration and invasion by altering AKT/mTOR/Rac1 signaling.

To determine the mechanism by which hsa-miR-204 may exhibit its tumor growth and metastasis suppressor activity, the effect of hsa-miR-204 on AKT/mTOR signaling was examined in light of BDNF having been shown previously to activate AKT pathway (Troca-Martin, et al., 2010); in addition, selective activation of AKT by mTOR has been shown to regulate cancer cell migration and invasion. Interestingly, hsa-miR-204 overexpression resulted in reduced activity of AKT and mTOR downstream targets 4E-BP1 and S6 (FIG. 5A). 4E-BP1 is a translation inhibitor that dissociates from eIF4E upon phosphorylation to allow protein translation, and S6 is a ribosomal protein whose phosphorylation facilitates assembly of the ribosome and consequent translation of mRNA. AKT controls cell invasiveness by regulating multiple processes that are involved in actin organization, cell-to-cell adhesion, and cell motility (Kim, et al., 2011; Grille, et al., 2003; Enomoto, et al., 2005).

Figures 5B, 5C:
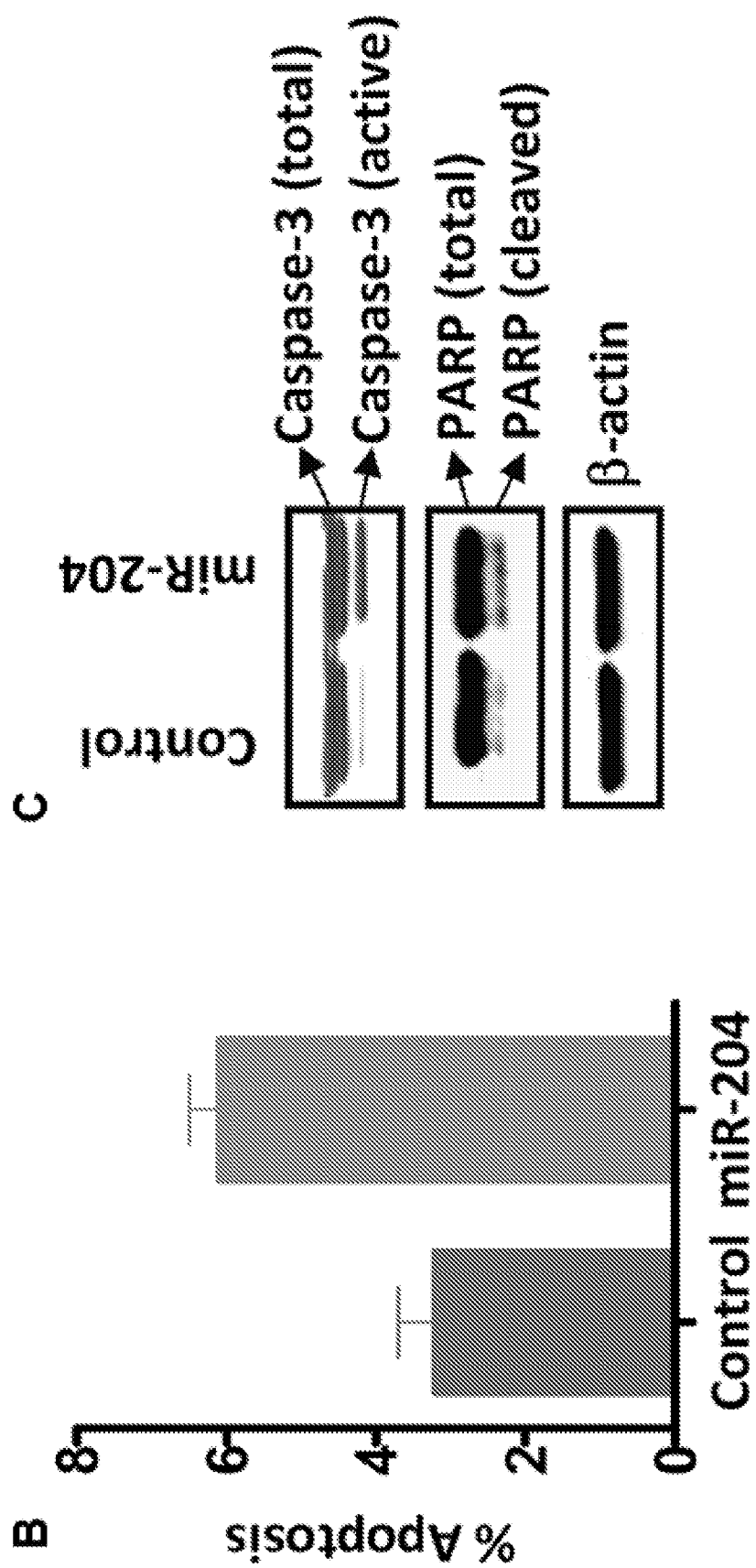

To examine whether miR-204 may play a direct role in this process, the effect of hsa-miR-204 overexpression on the activation of the small G protein Rac1 was assessed. The small G protein Rac1 functionally interacts with AKT/mTOR and is reported to play an important role in cell migration and actin reorganization upon induction with BDNF (zadran, et al., 2010) or epidermal growth factor (EGF) (Kim, et al., 2011). Stimulation of MDA-MB-231 cells (and SKOV3 or HEK-293 cells) with BDNF or EGF induced membrane ruffling, and this stimulation caused Rac1 to be translocated to the ruffling region (data not shown). In contrast, membrane ruffling and Rac1 translocation were not observed in cells overexpressing hsa-miR-204 when induced with BDNF or EGF (data not shown). Evasion of apoptosis, which is critical for tumor growth and progression (Hanahan, et al., 2000) could be another mechanism central to oncogenesis in cancers exhibiting loss of hsa-miR-204. Moreover, increased AKT/mTOR activity has also been associated with decreased apoptosis in cancers (Krishnan, et al., 2006). Indeed, hsa-miR-204 overexpression caused a significant increase in the levels of both activated caspase-3 and polyADP ribose polymerase (PARP), indicators of irreversible damage to the integrity of the cell and genome, with a resultant increase in apoptotic activity (FIGS. 5B & 5C). Taken together, these findings suggest that loss of hsa-miR-204 promotes tumor cell growth, migration and invasion by activating its target genes that are known regulators of oncogenic signaling cascade.

G. High-throughput Functional Screening.

Hsa-miR-204 is seen to be not only a tumor suppressor but also a miRNA that sensitizes drug resistant breast cancers to the chemotherapy drug paclitaxel.

To identify miRNAs that may sensitize paclitaxel resistant TNBC cells to paclitaxel, an unbiased and comprehensive approach was taken: a library of 974 chemically synthesized miRNA inhibitors was used in a high-throughput screening platform both to identify miRNAs that reduce TNBC cell viability in the presence of a sub-lethal dose of paclitaxel (2 to 8 nM), a dose at which 80% of TNBC cells were still viable, and to validate selected candidates. TNBC cell line MDA-468 was used.

The inhibitors, each of which targets one of 974 human microRNAs, were arrayed in a one-inhibitor-one-well format on 96-well micro-titer plates. Transfections of paclitaxel-resistant MDA-468 cells were performed in sextuplicate for triplicate analysis in the presence (sub-lethal concentration) and the absence of drug. Cells were subjected to a 72-hour exposure to drug at or below the $IC_{20}$, as derived from 5-day MTS assays. Cell viability was measured using CellTiter-Glo Viability Assay (Promega).

Figure 6:
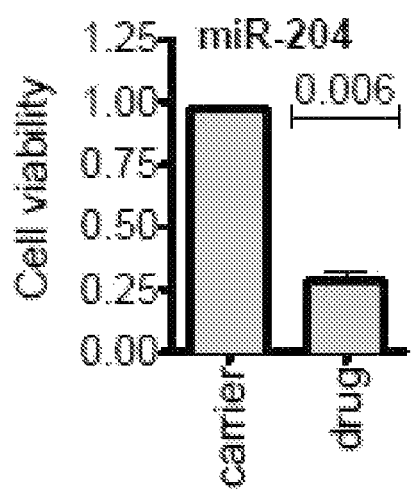
FIG. 6. Screen in which 974 inhibitors were successfully assayed. The screen of MDA-468 cells with paclitaxel (Pac) yielded 47 miRNAs sensitizers with a viability ratio (v.r.)<0.85. Of these, 10 miRNAs were significant at the p<0.05 level. Applying criteria noted to the screen resulted in the selection of sensitizer and de-sensitizer miRNAs. One of these miRNAs, sensitizer hsa-miR-204 (miR-204), when overexpressed, generated significantly reduced viability of MDA-468 cells in the presence of paclitaxel relative to control.

Raw values were normalized to internal reference control samples (positive and negative controls) on each plate to permit plate-to-plate comparisons. Each miRNA inhibitor is assigned a viability ratio-calculated as mean viability in paclitaxel divided by mean viability in the absence of drug (meanpac/meancarrier). In a high-throughput screen, the number of statistical comparisons significantly exceeds that of the biological replicates. For each miRNA inhibitor, a two sample t-test (with pooled variance) was performed to determine whether there is a significant difference between the mean values under the two experimental conditions (presence and absence of drug). Resulting raw p values were inflated based on their rank in the distribution of all p-values-based on the Benjamini-Hochberg method of controlling the false discovery rate (FDR). This protocol has been applied successfully in a genome-wide RNAi-based synthetic lethal screening study, where it identified a highly reproducible list of hits 18 and in the current screens (FIG. 6).

This screen resulted in identification of different categories of miRNAs: (1) De-sensitizers: miRNAs that, when inhibited, decreased cell viability (indicating that, when overexpressed, these miRNAs will support cell viability) in the presence of paclitaxel when compared to carrier; (2) Sensitizers: miRNAs that, when inhibited, increased cell viability (indicating that, when overexpressed, these miRNAs will decrease cell viability) in the presence of paclitaxel when compared to carrier; and (3) Drug-neutral: miRNAs that, when inhibited, had no significant effect on cell viability when compared between paclitaxel and carrier.

One sensitizer, hsa-miR-204, when inhibited, showed the highest magnitude of an increase in cell viability in paclitaxel-treated TNBC cells when compared to untreated carrier-maintained cells. As shown in FIG. 6, overexpression of sensitizer hsa-miR-204 resulted in a significant (more than approximately four-fold; P=0.006) decrease in TNBC cell viability in the presence of sub-lethal dose of paclitaxel when compared with untreated (carrier) control.

H. Ezrin

The inventors have also identified hsa-miR-204 binding to ezrin RNA, and specifically binding of the sequence 3'-UUUCCCUU-5' in the seed area of hsa-miR-204 to the corresponding 5'-AAAGGGAA-3' sequence in the ezrin 3'-UTR region. Ezrin is a member of the ezrin/radixin/moesin (ERM) family, and it promotes cytoskeletal reorganization by coupling functions of the plasma membrane and actin cytoskeleton of the cell. Ezrin has been implicated in tumor growth and metastasis of several adult and pediatric tumors, and strong multifocal expression of ezrin has been associated with poor prognoses for several tumors. P-glycoprotein binds to ezrin at amino acid residues 149 through 242 in the ferm domain and plays a key role in the multidrug resistance of human osteosarcoma.

Figure 7:
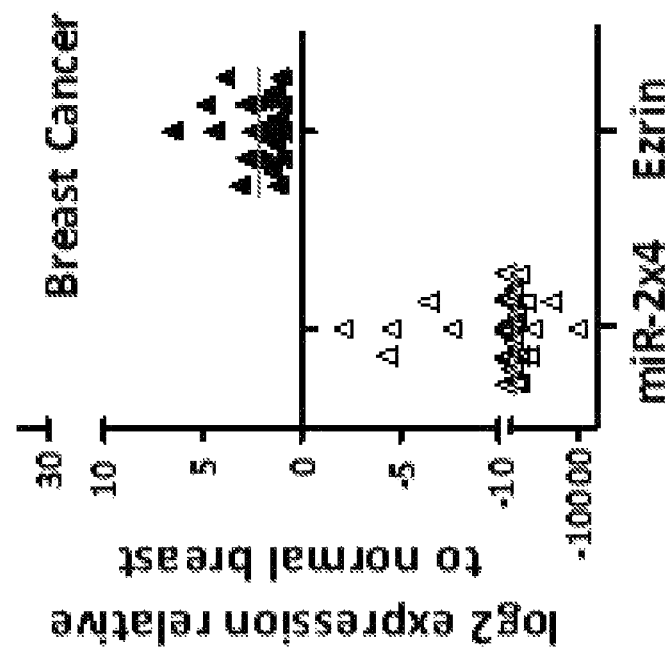
FIG. 7. Inverse correlation in expression between hsa-miR-204 (miR-2×4) and its target genes BDNF and Ezrin.
Figure 7:
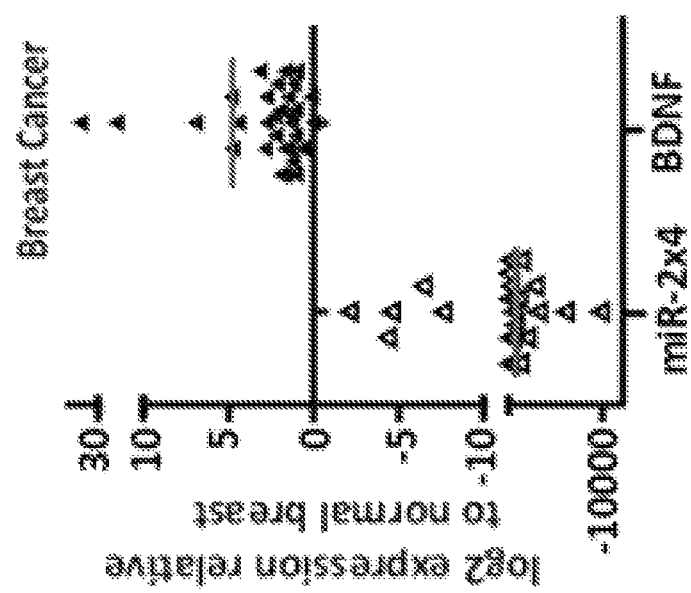
Figure 8:
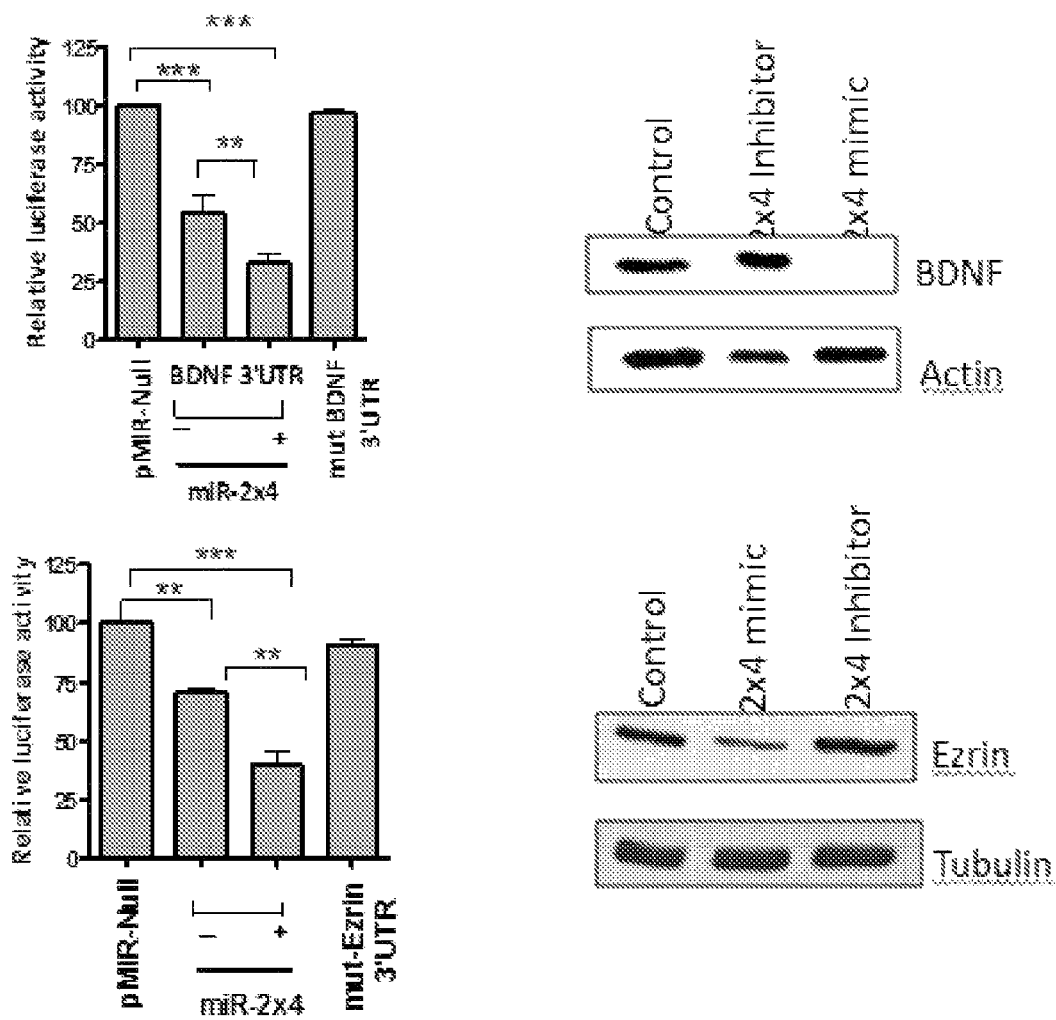
FIG. 8. BDNF expression and ezrin expression are bona fide targets of hsa-miR-204 (miR-2×4).

As is the case for the inverse correlation in expression of hsa-miR-204 and BDNF loci (FIGS. 4A, 4B, 4C, 4E, 4F, and 4G), there is an inverse correlation between expression of hsa-miR-204 and ezrin loci (FIG. 7). As is the case for BDNF expression, ezrin expression is a bona fide target of hsa-miR-204 (FIG. 8).

I. Additional Considerations

Many miRNAs associated with cancers are known to be localized to genomic fragile sites (Calin, et al., 2004). However, surprisingly little is known about the functional importance of regions with chromosomal aberrations containing miRNAs. It is likely that initial genetic screens that aimed at discovering chromosomal abnormalities (with typically lower comparative genomic hybridization resolution) overlooked changes in genomic regions containing miRNAs. Because miRNAs influence several genes in one or more pathways that regulate cell growth and apoptosis and contribute to tumor formation when deregulated, a closer scrutiny of smaller genomic regions encoding miRNAs may provide important insights into the mechanism of tumorigenesis. Most miRNAs are proposed to be downregulated in cancers, and microdeletion of genetic regions containing specific miRNAs may be an occurrence that plays an important role in the development and progression of human cancers.

Evidence is provided herein that hsa-miR-204, which acts as a potent tumor growth and metastasis suppressor, is somatically lost in some human cancers. That hsa-miR-204 regulates the expression and function of the pro-angiogenic protein BDNF and its receptor TrkB in tumors is demonstrated, as well as that loss of hsa-miR-204 promotes BDNF (or EGF)-induced cancer cell migration and invasion by activating AKT/mTOR pathway leading to Rac1 translocation and actin reorganization. Because AKT and Rac1 require each other for their activation (Kim, et al., 2011; Higuchi, et al., 2001), these findings suggest that loss of hsa-miR-204 expression in human tumors may induce the positive feedback loop between BDNF/AKT1 and Rac1 during growth factor-induced cancer cell migration and invasion. In support of this, EGF has been shown to activate AKT and facilitate Rac1 translocation to the cell membrane, and crosstalk between EGFR and TrkB has been shown to induce cancer cell migration (Qiu, et al., 2006). Moreover, response to EGF is a key step during cancer cell invasion and is directly linked with metastasis (Wyckoff, et al., 2004). In addition to cancer cell migration and invasion, activation of BDNF/TrkB signaling may also contribute to evasion of apoptosis in hsa-miR-204 depleted cells as BDNF/TrkB overexpression has been linked with stabilization and activation of AKT resulting in decreased apoptosis (Siu, et al., 2009). Consistent with this, these results demonstrate that hsa-miR-204 overexpression results in reduced phosphorylation and activation of mTOR downstream targets 4E-BP1 and S6 kinase.

Figure 12:
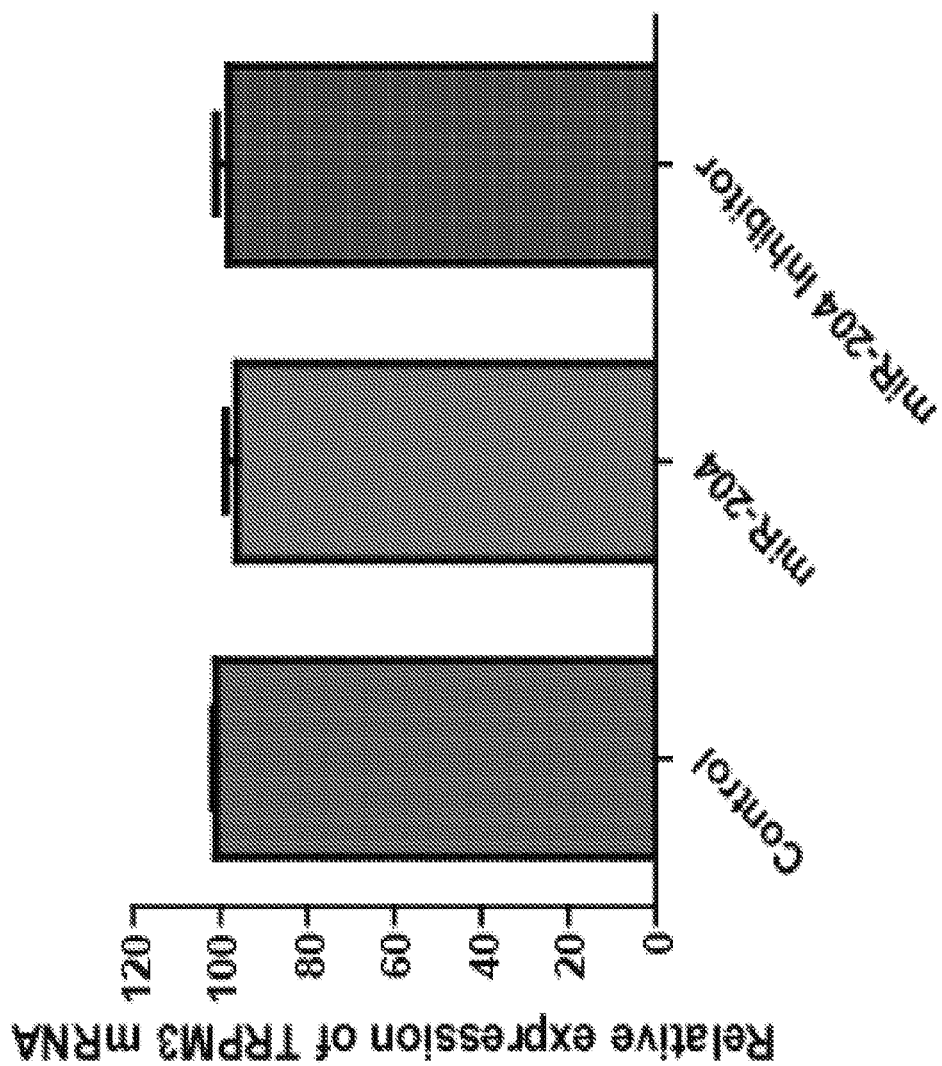
FIG. 12. Hsa-miR-204 (miR-204) does not affect TRPM3 levels.

Because hsa-miR-204 resides within the transient receptor potential cation channel member 3 (TRPM3) gene, which is a member of transient receptor potential channels family of proteins, and these proteins are known to be important for cellular calcium signaling and homeostasis, the speculation is tempting that the phenotypes associated with the genomic loss of chromosomal loci containing hsa-miR-204 may also be contributed by the host gene TRPM3. But results herein showing suppression of tumor growth and metastasis following introduction of hsa-miR-204 alone, with no change in the levels of TRPM3 gene in hsa-miR-204 mimic or inhibitor overexpressing cancer cells (FIG. 12). This clearly suggests that the hsa-miR-204-associated tumor suppressor phenotype is not mediated through TRPM3. However, the possibility cannot be excluded that hsa-miR-204 and its host gene TRPM3 act synergistically to regulate suppression of tumor growth as well as of tumor cell migration and invasion. Because a definite role for TRPM3 in tumorigenesis has not been reported, a detailed study examining TRPM3's potential tumor suppressor role and its synergistic effects with hsa-miR-204 (if any) may be subjects of future investigations.

Taken together, the findings herein suggest that genetic loci containing specific miRNA may play a causal role in cancer growth and metastasis by regulating key oncogenic pathways. The ability of hsa-miR-204 to target BDNF/TrkB, which have significant roles in normal cellular processes and are overexpressed in aggressive cancers, indicates that hsa-miR-204 may control key regulatory mechanisms, and that the dysregulation of such control can predispose normal developmental/differentiation events to undergo transformation. Therefore, strategies aimed at using hsa-miR-204 in therapeutic regimens will have the advantage of reversing inappropriately activated steps in cancer cells to a more normal state. The identification herein of hsa-miR-204 as a potent tumor suppressor-along with demonstration herein of its therapeutic potential and negligible hepatotoxicite-establishes a strong rationale for developing hsa-miR-204 as a key component of a viable therapeutic regimen to treat cancers.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Many of the following examples provide additional detail on exemplary materials and methods.

Example 1

Normal and Tumor Tissue Samples and Cell Lines

Cell lines representing pediatric renal tumors (HEK-293; embryonal kidney cell line), ovarian cancer (SKOV3) and breast cancer (MDA-MB-231) used for experiments were cultured according to ATCC protocols. Seventy-six pediatric renal tumors and normal matched kidney were acquired from the Children's Oncology Group (Arcadia, Calif.). Eleven advanced stage ovarian tumors and five normal ovarian tissues were obtained from UT MD Anderson Cancer Center (Houston, Tex.). Fifteen breast cancer tissues and normal matched tissues were obtained from UT Health Science Center (San Antonio, Tex.).

Example 2

RNA and Protein Analysis

Total RNA was extracted from tumors and normal tissues, as well as all cell lines, and was subjected to qRT-PCR analysis, as described previously (Imam, et al., 2010). Western blot analysis was performed as described previously (Imam, et al., 2010). Antibodies to β-actin (AC-74-A5316) and α-tubulin (T6199) were purchased from Sigma Aldrich. Antibody to BDNF was purchased from Santa Cruz, other antibodies including antibodies specific for caspase-8 (IC12-9746), caspase-3 (8G10-9665), caspase-9 (9502), PARP (9542S), AKT (9272), phospho-AKT (9271), S6 ribosomal protein (2217), and phospho-S6 ribosomal protein (5G10-2211S) were purchased from Cell Signaling.

Example 3

Genomic PCR Assay

Genomic DNA from pediatric renal tumors (n=38), and advanced stage (III and IV) ovarian cancers and matched normal renal (n=38) and ovarian (n=4) tissues were isolated with the DNeasy Genomic DNA Extraction Kit (Qiagen). For genomic analysis of hsa-miR-204, the $2^{\Delta\Delta ct}$ method was adapted using SYBR Green-based quantitative PCR (qRT-PCR) as described (Varambally, et al., 2008). Briefly, 25 ng of genomic DNA was used as template to amplify the hsa-miR-204 locus. A representative control tissue sample was used in every assay as a calibrator to which every sample was compared, to obtain a relative quantitation (RQ) value. Genomic DNA from a normal male sample (1×) and a normal female sample (2×) (Promega) was used to compare the levels of phosphoglycerate kinase 1 (PGK1) and five X-chromosome specific miRNAs-hsa-miR-424, hsa-miR-503, hsa-miR-766, hsa-miR-222 and hsa-miR-221—to calibrate the extent of loss in the various miRNA loci. RQ values for these regions in male genomic DNA were assessed using the non-X-chromosome TATA binding protein (TBP) gene as the reference. Based on its ability to separate two distinct data populations, an RQ value of 0.5 and below was considered as loss of at least one copy of a genomic locus.

Example 4

High-Resolution miRNA Comparative Genomic Hybridization (CGH) Assay

MiRNA CGH analysis was performed on the genomic DNA isolated from pediatric renal tumor samples using an Agilent custom-designed microarray as per the manufacturer's protocol. Custom arrays were designed based on the Agilent 2×105K Human Whole Genome Genomic Microarray using Agilent's eArray program (available online at earray.chem.agilent.com/earray), with additional probes that cover all miRNA regions (200 bp before, within and after of each miRNA from miRBase v13, with triplicate probes to enhance reliability). Array CGH data analysis was performed with Nexus Copy Number (BioDiscovery) for DNA alteration quantification. Upon determination of samples with or without copy number alteration at specific miRNA sites, all array CGH data was loaded into MATLAB for a composite graphical display. Array CGH showing position of the probes and normalized copy numbers have been submitted to GEO/NCBI data base (GSE28397).

Example 5

Meta-Analysis

Meta-analysis was performed on a public domain high density CGH dataset on 354 ovarian cancers (obtained from The Cancer Genome Atlas (TCGA) Project, located online at <cancergenome.nih.gov>) and 35 breast cancers (GSE15130). Array CGH data for all tumors imported into Nexus Copy Number. Threshold for copy number loss was set to log 2-0.5 (more stringent than the default setting of log 2-0.2). Meta-analysis for gene expression analysis was performed on a public domain gene expression dataset (GSE22820) from the GEO/NCBI. Differential expression of TRPM3 (the locus containing miR-204) in breast cancer samples was determined by first performing RMA/quantile normalization and then comparing to normal adjacent tissues within the same data set.

Example 6

Gene Expression Analysis

Human gene expression microarray data were generated using the Agilent Human Whole Genome 4×44K array (Agilent Technologies). Total RNA isolated from HEK-293 cells transfected with miR-204 was co-hybridized with RNA from HEK-293 cell transfected with scrambled oligo (control) with dye-swap replicates, following the manufacturer's protocol. Relative gene expression ratios were extracted with Agilent's Feature Extraction software (version 9.5.3.1, Agilent Technologies). Quantile normalization was performed with the MATLAB Bioinformatics Toolbox (R2009a, Mathworks). To determine differential expression of genes, the Student's t-test was applied to the normalized expression data. Signature gene sets were selected based on an FDR-adjusted P<0.05 (Benjamini-Hochberg) and a fold change>2. Differential gene expression dataset has been deposited in GEO/NCBI data base (GSE 28400).

Example 7

Plasmid Construction

For the pMIR-BDNF 3' UTR construct, the 3'-UTR segment of the BDNF gene was amplified and sub-cloned downstream of the luciferase gene in the pMIR-REPORT vector (Ambion) at the HindIII and SpeI sites. For the pSilencer-miR-204 construct, an approximately 500 bp pri-miR-204 genomic sequence was amplified and cloned into the BamHI and HindIII sites of the pSilencer 4.1 Puro vector (Ambion).

Example 8

Cell Growth and Soft Agar Assay

Cell growth and soft agar colony formation assay using pSilencer-miR-204 and pSilencerscramble (control) stable cell lines were performed as described previously (Imam, et al., 2010).

Example 9

Tumorigenicity Assays in SCID Mice

Two million HEK-293 cells stably overexpressing either pSilencer-miR-204 or pSilencer-scramble were injected into the renal capsules of 9 RAG2$^{-/-}$, γc$^{-/-}$ SCID male mice (Taconic) and 9 control mice. Tumor volume was assessed 24 d after transplantation, using the formula π/6×(L×D×W), where L is tumor length, D is depth and W is width. Six micrometer paraffin embedded tumor sections were stained with hematoxylin and eosin. All experimental procedures involving animals were performed according to institutional ethical guidelines.

Example 10

Transwell Cell Migration and Basement Membrane Matrix Invasion Assay

Transwell cell migration assays were performed as previously described (Imam, et al., 2010). Invasion assays were performed with MDA-MB-231 cells transfected with 75 nM miR-204 mimic or negative control mimic, then further transfected for 48 h with 75 nM miR-204-specific inhibitor or 25 ng of pBluescript KS$^+$ control, as described below. Forty-eight hours post-transfection, cells were seeded onto the inserts of 24-well transwell plates precoated with Matrigel (1 mg/mL) (BD Biosciences). Serum-containing media and fibronectin (5 μg/mL) were added to the lower chamber as chemoattractants. After 24 h incubation, cells on transwell inserts were washed, fixed, and non-invading cells and EC matrix were gently removed with a cotton swab. Invasive cells located on the lower side of the chamber were stained with crystal violet (0.1%), air dried and photographed as described (Imam, et al., 2010).

Example 11

Therapeutic Experiments 100,000 MDA-MB-231-GFP-luc cells were injected into the tail vein. Starting from 7 d after tumor cell injection, hsa-miR-204 (n=6) or hsa-miR-204 mutant (n=6) oligos complexed with RNALancerII in vivo delivery formulation (Bioo Scientific) were injected every 5 d for 30 d at a rate of 1 mg of oligo per kg of body weight. All animals were sacrificed after the sixth injection. Lungs were fixed and analyzed for metastatic foci. Lung images were captured using fluorescence microscope (for GFP$^{+ve}$ and luc$^{+ve}$ foci). Livers were also harvested to assess metastasis and hepatoxicity in hsa-miR-204 injected mice.

Example 12

Apoptosis Assays

Annexin V/PI staining on HEK 293 or HeLa cells transfected with 75 nM hsa-miR-204 mimic or negative control mimic was performed in triplicate wells using the FITC Annexin V Apoptosis Detection Kit (BD Pharmingen) as described previously (32).

Example 13

Immunofluorescence

Cells were fixed with 4% paraformaldehyde and permeabilized with 0.2% Triton X-100 for 15 min at room temperature (RT), then washed with phosphate-buffered saline (PBS) and blocked with 10% goat serum in PBS for 45 min at RT. Cells were incubated with Rac1 mouse monoclonal antibody (ab33186, Abcam) diluted in PBS for 2 h at RT. Cells were washed three times before incubating for 1 h at RT with 1:200 Alexa Fluor 647 and Alexa Fluor 488 phalloidinconjugated secondary antibodies (A12379, Invitrogen, Molecular Probes). After three washes, cells were mounted on glass slides in Aqua-Poly/Mount medium containing DAPI (Polysciences). Photomicrographs were taken at 200× magnification on a Nikon Eclipse TE2000-U microscope.

Example 14

Statistical Analysis

All values and error bars in graphs are mean±SEM; respective n values are indicated in figure legends; P-values are determined by two-tailed Student's t-tests.

Figure 13:
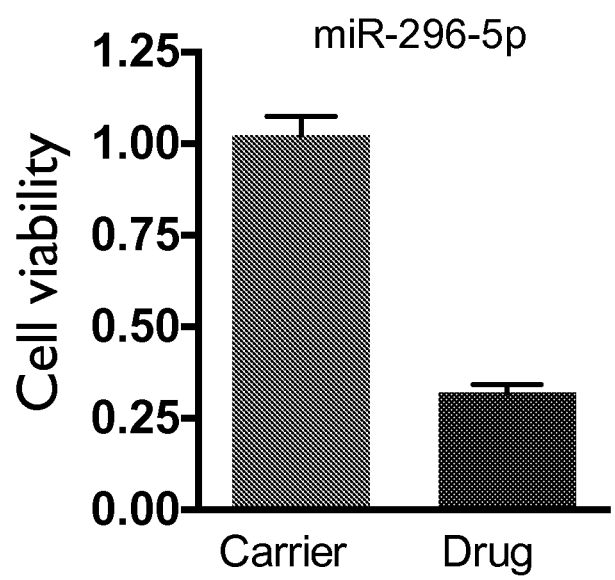
FIG. 13 miR-296-5p inhibition sensitizes paclitaxel response in triple negative breast cancers.

Example 15 miR-296-5p Inhibition Sensitizes Paclitaxel Response in Triple Negative Breast Cancers Triple negative breast cancer cells were transfected with scramble control or miR-296-5p inhibitor for 3-days followed by treatment with either carrier or 8 nM Paclitaxel for two more days. Cell viability was compared between carrier and drug treated miR-296-5p transfected cells using Cell-Titer-Glo (Promega Inc.). miR-296-5p inhibition significantly reduced the cell viability in the presence of paclitaxel. Bar graph depicts percentage of TNBC cell viability in control and miR-296-5p transfected cells treated with vehicle control (DMSO) or paclitaxel (8 nM). FIG. 13.

Example 16 miR-296-5p Inhibits Triple Negative Breast Cell Migration and Invasion

Figure 14:
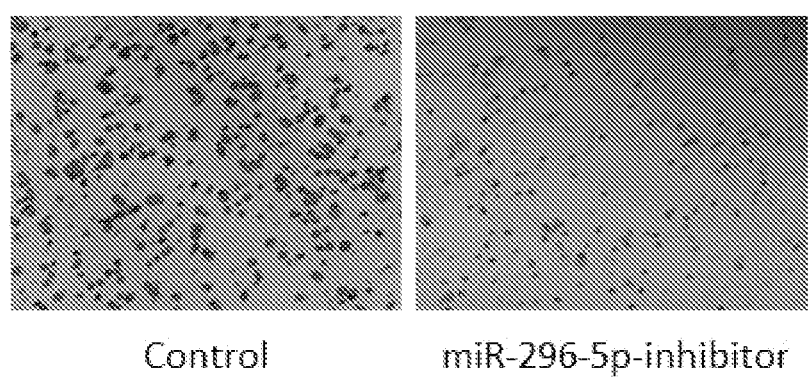
FIG. 14 miR-296-5p inhibits triple negative breast cell migration and invasion.

Triple negative breast cancer cells were transfected with scramble control or miR-296-5p inhibitor for 48 hours. At 48 h after transfection, cells were trypsinized, resuspended in serum-free media and loaded into the top of 3 µm-pore-sized Transwell chambers (Corning, Corning, N.Y., USA). Serum-containing medium was placed in the bottom chamber as a chemoattractant and cells were incubated at 37° C. and allowed to migrate through the chemotaxis chamber for 24 h. The migrated cells at the bottom of the chamber were fixed with 10% formalin and stained with 0.4% crystal violet for 3 h. Experiments were repeated in triplicate and migrated cells were counted microscopically miR-296-5p inhibitor transfected cells had significantly lower migratory capability when compared to control transfected cells. Representative image shows invaded cells. Picture was taken using Nikon microscope. FIG. 14.

Example 17

Efficacy of Treatment

Figure 15:
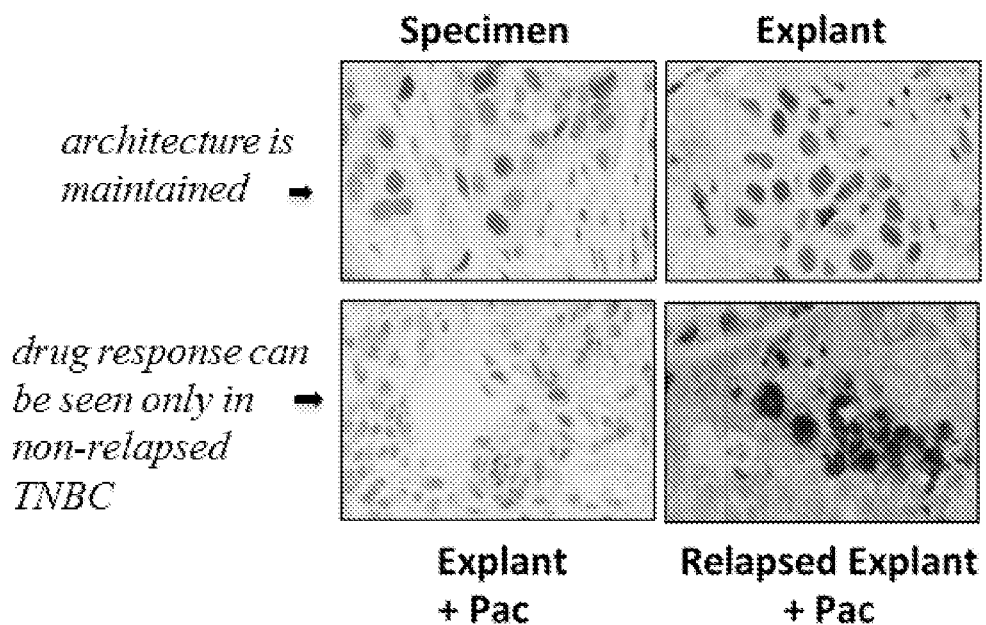
FIG. 15 To further establish the efficacy of these miRNAs in treating TNBC, we cultured tumor tissues chunks (1 mm3) on the dental sponge. The tumor implant maintained the architecture of the tumor as shown in top two panels.

To further establish the efficacy of these miRNAs in treating TNBC, we used ex-vivo tumor explant model. Freshly excised breast cancer tissues were dissected into 1 mm$^3$ specimens, placed on hydrated gelatin sponge in explant media supplemented with hydrocortisone and insulin at 37° C. in the $CO_2$ incubator. Tumor explants from TNBC patients were treated with paclitaxel and tissues were gently removed, fixed in 10% neutral buffered formalin and processed for paraffin blocks. IHC analyses were conducted to determine the Ki67 levels. IHC of surgical specimens and explants reveal that explants retain the tissue architecture and proliferation properties of the original surgical specimen. Expectedly, paclitaxel treatment of explant revealed inhibition of Ki67 staining in non-relapsed TNBC, while advanced stage TNBC was not responsive to the paclitaxel. FIG. 15.

Example 18

Liposome Formulation

Figure 16:
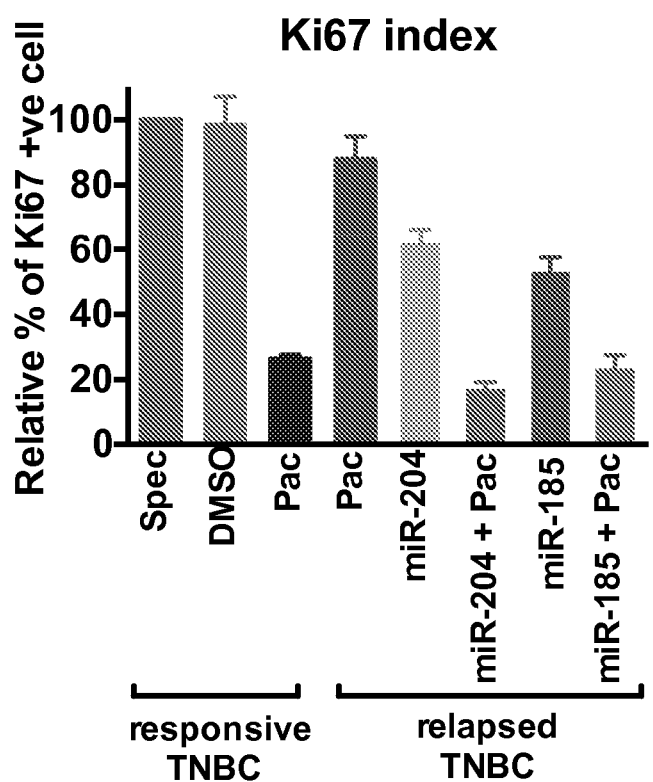
FIG. 16 Addition of sensitizer miRNAs alone using liposome formulation resulted in killing of tumor cells.

Tumor explants growing on the gelatin sponge were treated with either sensitizer miRNA (75 nM) alone or paclitaxel (1 µM) alone or with miRNA (75 nM) and paclitaxel (1 µM) together. Treatment of paclitaxel (by adding in explant media) alone for 48 hours resulted in significant inhibition of Ki67 levels (indicating tumor cell proliferation) in responsive TNBC (early stage cancer). However, paclitaxel treatment did not result in significant change in the Ki67 levels in relapsed TNBC explants that are not responsive to paclitaxel Addition of sensitizer miRNA (75 nM) alone using liposome formulation for 48 hours resulted in modest inhibition of Ki67 levels (indicating tumor cell proliferation) in tumor explants from advanced stage TNBC. However, the effect was much more robust when sensitizer miRNA (75 nM) was used in combination with paclitaxel (1 µM). FIG. 16.

REFERENCES

The following references, to the extent that they provide exemplary procedural or other details supplementary to those set forth herein, are specifically incorporated herein by reference.

Albertson & Pinkel, Hum Mol Genet. 12 Spec. No. 2:R145-152, 2003.
Artzi, et al., BMC Bioinformatics. 9:39, 2008.
Au, et al., Cancer Lett. 281:151-161, 2009.
Bartel, Cell. 116: 281-297, 2004.
Bartels & Tsongalis, Clin Chem. 55:623-631, 2009.
Bayani, et al., Semin Cancer Biol. 17:5-18, 2007.
Brodeur, Nat Rev Cancer 3:203-216, 2003.
Calin, et al., Proc Natl Acad Sci USA 101:2999-3004, 2004.
Du, et al., Mol Cancer Res. 7:1234-1243, 2009.
Edsjo, et al., Lab Invest. 83:813-823, 2003.
Enomoto, et al., Dev Cell. 9:389-402, 2005.
Esquela-Kerscher & Slack, Nat Rev Cancer. 6:259-269, 2006.
Friedman, et al., Genome Res. 19(1):92-105, 2009
Grille, et al., Cancer Res. 63:2172-2178, 2003.
Guo, et al., Nature. 466:835-840, 2010.
Hanahan & Weinberg, Cell. 100:57-70, 2000.
Higuchi, et al., Curr Biol 11:1958-1962, 2001.
Imam, et al., Oncogene. 29:4971-4979, 2010.
Kim, et al., Oncogene. 30:2954-2963, 2011.
Krek, et al., Nat Genet. 37:495-500, 2005.
Krishnan, et al., Clin Exp Metastasis 23:227-236, 2006.
Lewin, Philos Trans R Soc Lond B Biol Sci. 351:405-411, 1996.
Lewis, et al., Cell. 120:15-20, 2005.
Liu, et al., BMC Genomics. 11 Suppl. 3:S12, 2010.
Nakagawara, et al., Mol Cell Biol. 14:759-767, 1994.
Qiu, et al., Int J Oncol 29:1003-1011, 2006.
Segal, et al., J Biol Chem. 271:20175-20181, 1996.
Shen, et al., Biologicals. 36:263-268, 2008.
Siu, et al., Expert Opin Ther Targets. 13:1169-1178, 2009.
Troca-Marin, et al., Mol Cell Neurosci. 43:308-314, 2010.
Varambally et al., Science. 322:1695-1699, 2008.
Wyckoff, et al., Cancer Res. 64:7022-7029, 2004.
Yue, et al., ACM International conference on Bioinformatics and Computational Biology, 2010.
Zadran, et al., J. Neurosci. 30:1086-1095, 2010.

The invention claimed is:

1. A method for reducing growth of cancer cells comprising administering an effective amount of a composition comprising hsa-miR-204 to a subject having or suspected of having cancer cells reduced in expression of hsa-miR-204, wherein the subject is further administered a composition comprising a second active agent before, after, and/or during administration of the composition comprising hsa-miR-204, and wherein cancer cells have become resistant to the second active agent.

2. The method of claim 1, wherein the cancer cells overexpress brain-derived neurotrophic factor (BDNF) and/or ezrin.

3. The method of claim 1, wherein the cancer cells are triple negative breast cancer (TNBC) cells, breast cancer cells other than TNBC cells, ovarian cancer cells, and/or pediatric renal tumor cells, or any combination thereof.

4. The method of claim 1, further comprising determining the level of hsa-miR-204 in the cancer cells wherein the level of hsa-miR-204 is reduced when compared to a control.

5. The method of claim 4, wherein the level of hsa-miR-204 in a blood sample obtained from the subject is determined.

6. The method of claim 1, wherein the second active agent comprises a cytotoxic chemotherapeutic, a nanobioconjugate, and/or a miRNA other than hsa-miR-204, or any combination thereof.

* * * * *

SEQUENCE LISTING

<160> NUMBER OF SEQ ID NOS: 50

<210> SEQ ID NO 1
<211> LENGTH: 32
<212> TYPE: RNA
<213> ORGANISM: Homo sapiens

<400> SEQUENCE: 1
ggcuacaguc uuucuucaug ugacucgugg ac        32

<210> SEQ ID NO 2
<211> LENGTH: 22

```
<212> TYPE: RNA
<213> ORGANISM: Homo sapiens

<400> SEQUENCE: 2
uucccuuugu cauccuaugc cu                                            22

<210> SEQ ID NO 3
<211> LENGTH: 17
<212> TYPE: RNA
<213> ORGANISM: Homo sapiens

<400> SEQUENCE: 3
gagaauauau gaaggag                                                  17

<210> SEQ ID NO 4
<211> LENGTH: 21
<212> TYPE: RNA
<213> ORGANISM: Homo sapiens

<400> SEQUENCE: 4
gcugggaagg caaagggacg u                                             21

<210> SEQ ID NO 5
<211> LENGTH: 18
<212> TYPE: RNA
<213> ORGANISM: Homo sapiens

<400> SEQUENCE: 5
ucaauuguca ucacuggc                                                 18

<210> SEQ ID NO 6
<211> LENGTH: 14
<212> TYPE: RNA
<213> ORGANISM: Homo sapiens

<400> SEQUENCE: 6 aggggggcgag ggau                                                    14

<210> SEQ ID NO 7
<211> LENGTH: 22
<212> TYPE: RNA
<213> ORGANISM: Homo sapiens

<400> SEQUENCE: 7
uggagagaaa ggcaguuccu ga                                            22

<210> SEQ ID NO 8
<211> LENGTH: 13
<212> TYPE: RNA
<213> ORGANISM: Homo sapiens

<400> SEQUENCE: 8 uggucccuc ccc                                                       13

<210> SEQ ID NO 9
<211> LENGTH: 22
<212> TYPE: RNA
<213> ORGANISM: Homo sapiens

<400> SEQUENCE: 9
aggggcuggc uuccucugg uc                                             22

<210> SEQ ID NO 10
```

```
<211> LENGTH: 11
<212> TYPE: RNA
<213> ORGANISM: Homo sapiens

<400> SEQUENCE: 10
cuucccuccc a                                                          11

<210> SEQ ID NO 11
<211> LENGTH: 25
<212> TYPE: RNA
<213> ORGANISM: Homo sapiens

<400> SEQUENCE: 11
ucaccuggcc augugacuug ugggc                                           25

<210> SEQ ID NO 12
<211> LENGTH: 22
<212> TYPE: RNA
<213> ORGANISM: Homo sapiens

<400> SEQUENCE: 12
uucccuuugu cauccuucgc cu                                              22

<210> SEQ ID NO 13
<211> LENGTH: 15
<212> TYPE: RNA
<213> ORGANISM: Homo sapiens

<400> SEQUENCE: 13
agggcucuga gcagg                                                      15

<210> SEQ ID NO 14
<211> LENGTH: 21
<212> TYPE: RNA
<213> ORGANISM: Homo sapiens

<400> SEQUENCE: 14
gcagggacag caaaggggug c                                               21

<210> SEQ ID NO 15
<211> LENGTH: 27
<212> TYPE: RNA
<213> ORGANISM: Homo sapiens

<400> SEQUENCE: 15
ucaguuguca cuucccacag cacggag                                         27

<210> SEQ ID NO 16
<211> LENGTH: 5
<212> TYPE: RNA
<213> ORGANISM: Homo sapiens

<400> SEQUENCE: 16 ccauu                                                                  5

<210> SEQ ID NO 17
<211> LENGTH: 22
<212> TYPE: RNA
<213> ORGANISM: Homo sapiens

<400> SEQUENCE: 17
acuguugcua auaugcaacu cu                                              22
```

-continued

```
<210> SEQ ID NO 18
<211> LENGTH: 16
<212> TYPE: RNA
<213> ORGANISM: Homo sapiens

<400> SEQUENCE: 18
guugaauaua aauugg                                                      16

<210> SEQ ID NO 19
<211> LENGTH: 22
<212> TYPE: RNA
<213> ORGANISM: Homo sapiens

<400> SEQUENCE: 19
aauugcacuu uagcaauggu ga                                               22

<210> SEQ ID NO 20
<211> LENGTH: 3
<212> TYPE: RNA
<213> ORGANISM: Homo sapiens

<400> SEQUENCE: 20 ugg                                                                     3

<210> SEQ ID NO 21
<211> LENGTH: 21
<212> TYPE: RNA
<213> ORGANISM: Homo sapiens

<400> SEQUENCE: 21
gggagccaaa ugcuuugcua g                                                21

<210> SEQ ID NO 22
<211> LENGTH: 22
<212> TYPE: RNA
<213> ORGANISM: Homo sapiens

<400> SEQUENCE: 22
agcugguaaa auggaaccaa au                                               22

<210> SEQ ID NO 23
<211> LENGTH: 15
<212> TYPE: RNA
<213> ORGANISM: Homo sapiens

<400> SEQUENCE: 23
cgacugucca augga                                                       15

<210> SEQ ID NO 24
<211> LENGTH: 22
<212> TYPE: RNA
<213> ORGANISM: Homo sapiens

<400> SEQUENCE: 24
uuuggucccc uucaaccagc ug                                               22

<210> SEQ ID NO 25
<211> LENGTH: 22
<212> TYPE: RNA
<213> ORGANISM: Homo sapiens

<400> SEQUENCE: 25
uagcugugca uugauggcgc cg                                               22
```

```
<210> SEQ ID NO 26
<211> LENGTH: 4
<212> TYPE: RNA
<213> ORGANISM: Homo sapiens

<400> SEQUENCE: 26 ggau                                                                       4

<210> SEQ ID NO 27
<211> LENGTH: 21
<212> TYPE: RNA
<213> ORGANISM: Homo sapiens

<400> SEQUENCE: 27
cuuuuugcgg ucugggcuug c                                                   21

<210> SEQ ID NO 28
<211> LENGTH: 23
<212> TYPE: RNA
<213> ORGANISM: Homo sapiens

<400> SEQUENCE: 28
uguuccucuc aacaguaguc agg                                                 23

<210> SEQ ID NO 29
<211> LENGTH: 22
<212> TYPE: RNA
<213> ORGANISM: Homo sapiens

<400> SEQUENCE: 29
aagcccuuac cccaaaaagu au                                                  22

<210> SEQ ID NO 30
<211> LENGTH: 2
<212> TYPE: RNA
<213> ORGANISM: Homo sapiens

<400> SEQUENCE: 30 cu                                                                         2

<210> SEQ ID NO 31
<211> LENGTH: 13
<212> TYPE: RNA
<213> ORGANISM: Homo sapiens

<400> SEQUENCE: 31
aggacccuuc cag                                                            13

<210> SEQ ID NO 32
<211> LENGTH: 21
<212> TYPE: RNA
<213> ORGANISM: Homo sapiens

<400> SEQUENCE: 32 agggccccccc cucaauccug u                                                  21

<210> SEQ ID NO 33
<211> LENGTH: 13
<212> TYPE: RNA
<213> ORGANISM: Homo sapiens

<400> SEQUENCE: 33
ugugccuaau uca                                                            13
```

<210> SEQ ID NO 34
<211> LENGTH: 22
<212> TYPE: RNA
<213> ORGANISM: Homo sapiens

<400> SEQUENCE: 34
gaggguuggg uggaggcucu cc                                              22

<210> SEQ ID NO 35
<211> LENGTH: 11
<212> TYPE: RNA
<213> ORGANISM: Homo sapiens

<400> SEQUENCE: 35
ugaagggcuc u                                                          11

<210> SEQ ID NO 36
<211> LENGTH: 18
<212> TYPE: RNA
<213> ORGANISM: Homo sapiens

<400> SEQUENCE: 36
gauggcugug aguuggcu                                                   18

<210> SEQ ID NO 37
<211> LENGTH: 22
<212> TYPE: RNA
<213> ORGANISM: Homo sapiens

<400> SEQUENCE: 37
uaaucucagc uggcaacugu ga                                              22

<210> SEQ ID NO 38
<211> LENGTH: 7
<212> TYPE: RNA
<213> ORGANISM: Homo sapiens

<400> SEQUENCE: 38 gauguuc                                                               7

<210> SEQ ID NO 39
<211> LENGTH: 22
<212> TYPE: RNA
<213> ORGANISM: Homo sapiens

<400> SEQUENCE: 39
ucacaguggu cucugggauu au                                              22

<210> SEQ ID NO 40
<211> LENGTH: 49
<212> TYPE: RNA
<213> ORGANISM: Homo sapiens

<400> SEQUENCE: 40
gugggagggc ccaggcgcgg gcagggguggg ggguggcaga gcgcugucc                49

<210> SEQ ID NO 41
<211> LENGTH: 21
<212> TYPE: RNA
<213> ORGANISM: Homo sapiens

<400> SEQUENCE: 41

-continued

```
cgggggcggg gccgaagcgc g                                              21

<210> SEQ ID NO 42
<211> LENGTH: 11
<212> TYPE: RNA
<213> ORGANISM: Homo sapiens

<400> SEQUENCE: 42
gcgaccguaa c                                                         11

<210> SEQ ID NO 43
<211> LENGTH: 21
<212> TYPE: RNA
<213> ORGANISM: Homo sapiens

<400> SEQUENCE: 43
uccuucugcu ccguccccca g                                              21

<210> SEQ ID NO 44
<211> LENGTH: 11
<212> TYPE: RNA
<213> ORGANISM: Homo sapiens

<400> SEQUENCE: 44
ugagaggccg c                                                         11

<210> SEQ ID NO 45
<211> LENGTH: 22
<212> TYPE: RNA
<213> ORGANISM: Homo sapiens

<400> SEQUENCE: 45
accuugccuu gcugcccggg cc                                             22

<210> SEQ ID NO 46
<211> LENGTH: 13
<212> TYPE: RNA
<213> ORGANISM: Homo sapiens

<400> SEQUENCE: 46
gugcacccgu ggg                                                       13

<210> SEQ ID NO 47
<211> LENGTH: 20
<212> TYPE: RNA
<213> ORGANISM: Homo sapiens

<400> SEQUENCE: 47
ccccagggcg acgcggcggg                                                20

<210> SEQ ID NO 48
<211> LENGTH: 14
<212> TYPE: RNA
<213> ORGANISM: Homo sapiens

<400> SEQUENCE: 48
ggcggcccua gcga                                                      14

<210> SEQ ID NO 49
<211> LENGTH: 29
<212> TYPE: RNA
<213> ORGANISM: Homo sapiens

<400> SEQUENCE: 49
```

```
uucucguccc aguucuuccc aaaguugag                                      29

<210> SEQ ID NO 50
<211> LENGTH: 19
<212> TYPE: RNA
<213> ORGANISM: Homo sapiens

<400> SEQUENCE: 50
aaaagcuggg uugagagga                                                 19
```